US008663657B2

(12) United States Patent  
Fuller

(10) Patent No.: US 8,663,657 B2  
(45) Date of Patent: Mar. 4, 2014

(54) NUCLEIC ACID CONSTRUCTS

(75) Inventor: James Fuller, Cranberry Township, PA (US)

(73) Assignee: PowderJect Vaccines, Inc., Wilmington, DE (US)

( * ) Notice: Subject to any disclaimer, the term of this patent is extended or adjusted under 35 U.S.C. 154(b) by 1635 days.

(21) Appl. No.: 10/575,087

(22) PCT Filed: Oct. 11, 2004

(86) PCT No.: PCT/GB2004/004279  
§ 371 (c)(1),  
(2), (4) Date: May 22, 2006

(87) PCT Pub. No.: WO2005/035771  
PCT Pub. Date: Apr. 21, 2005

(65) Prior Publication Data  
US 2008/0160048 A1    Jul. 3, 2008

Related U.S. Application Data

(60) Provisional application No. 60/509,936, filed on Oct. 10, 2003.

(51) Int. Cl.

| | |
|---|---|
| *A61K 31/70* | (2006.01) |
| *C12N 15/11* | (2006.01) |
| *C12N 15/00* | (2006.01) |
| *A61K 39/00* | (2006.01) |
| *A61P 43/00* | (2006.01) |
| *C12N 15/87* | (2006.01) |
| *A61K 9/50* | (2006.01) |

(52) U.S. Cl.  
USPC ... 424/275.1; 536/23.5; 536/23.7; 536/23.72; 536/24.1; 435/320.1; 435/455; 424/184.1; 424/277.1; 604/48

(58) Field of Classification Search  
USPC ............ 424/186.1, 139.1, 85.4, 232.1, 93.71; 435/5, 320.1, 6.13, 325; 514/86, 46, 514/291, 44, 1.1; 530/387.9, 350; 536/23.72  
See application file for complete search history.

(56) References Cited

U.S. PATENT DOCUMENTS

| | | | |
|---|---|---|---|
| 5,100,792 A | 3/1992 | Sanford et al. | |
| 5,168,062 A | 12/1992 | Stinski | |
| 5,385,839 A | 1/1995 | Stinski | |
| 5,630,796 A | 5/1997 | Bellhouse et al. | |
| 5,865,796 A | 2/1999 | McCabe | |
| 6,110,707 A | 8/2000 | Newgard et al. | |
| 6,165,477 A * | 12/2000 | Ivy et al. ................ | 424/218.1 |
| 6,218,140 B1 | 4/2001 | Fleckenstein et al. | |
| 2003/0124523 A1* | 7/2003 | Asselbergs et al. ............. | 435/6 |
| 2003/0175711 A1* | 9/2003 | Renner et al. .................. | 435/6 |
| 2010/0221349 A1* | 9/2010 | Fuller ............................ | 424/490 |

FOREIGN PATENT DOCUMENTS

| | | |
|---|---|---|
| CA | 2425852 A | 4/2002 |
| EP | 0323997 B1 | 7/1989 |
| WO | WO 95/20660 | 8/1995 |
| WO | WO 99/03981 | 1/1999 |
| WO | WO 99/03981 A | 1/1999 |
| WO | WO 99/61472 | 12/1999 |
| WO | WO 00/23592 | 4/2000 |
| WO | WO 00/23592 A | 4/2000 |
| WO | WO 01/58483 A2 | 8/2001 |
| WO | WO 02/31137 A | 4/2002 |
| WO | WO 02/31137 A2 | 4/2002 |
| WO | WO 02/36792 A | 5/2002 |
| WO | WO 02/36792 A2 | 5/2002 |
| WO | WO 02/094313 A | 11/2002 |
| WO | WO 02/094313 A2 | 11/2002 |
| WO | WO 03/004055 A2 | 1/2003 |
| WO | WO 03/011334 A | 2/2003 |
| WO | WO 03/011334 A1 | 2/2003 |
| WO | WO 2005/035779 A2 | 4/2005 |
| WO | WO 2006/082398 A2 | 8/2006 |

OTHER PUBLICATIONS

Scharton-Kersten et al. Transcutaneous Immunization with Bacterial ADP-Ribosylating Exotoxins, Subunits, and Unrelated Adjuvants. Infect Immun. Sep. 2000; 68(9): 5306-5313.*  
Palmiter et al. Heterologous introns can enhance expression of transgenes in mice. Proc Natl Acad Sci U S A. Jan. 15, 1991;88(2):478-82.*  
Dean et al. Sequence requirements for plasmid nuclear import.Exp Cell Res. Dec. 15, 1999;253(2):713-22.*  
Li et al. Muscle-specific enhancement of gene expression by incorporation of SV40 enhancer in the expression plasmid. Gene Ther. Mar. 2001;8(6):494-7.*  
Moriarty et al. Expression of the hepatitis B virus surface antigen gene in cell culture by using a simian virus 40 vector. Proc Natl Acad Sci U S A. Apr. 1981;78(4):2606-10.*  
Nott et al. A quantitative analysis of intron effects on mammalian gene expression. RNA. May 2003;9(5):607-17.*  
Bulla and Siddiqui. The hepatitis B virus enhancer modulates transcription of the hepatitis B virus surface antigen gene from an internal location. J Virol. Apr. 1988;62(4):1437-41.*  
Protzer et al. Interferon gene transfer by a hepatitis B virus vector efficiently suppresses wild-type virus infection. Proc Natl Acad Sci U S A. Sep. 14, 1999;96(19):10818-23.*  
GenBank AF143308, Hepatitis B virus clone WB1254, complete genome, 1999.*  
Vannice JL, Levinson AD. Properties of the human hepatitis B virus enhancer: position effects and cell-type nonspecificity. J Virol. Apr. 1988;62(4):1305-13.*  
Macklin MD, McCabe D, McGregor MW, Neumann V, Meyer T, Callan R, Hinshaw VS, Swain WF. Immunization of pigs with a particle-mediated DNA vaccine to influenza A virus protects against challenge with homologous virus. J Virol. Feb. 1998;72(2):1491-6.*  
Swain We, Heydenburg Fuller D, Wu MS, Barr LJ, Fuller JT, Culp J, Burkholder J, Dixon RM, Widera G, Vessey R, Roy MJ. Tolerability and immune responses in humans to a PowderJect DNA vaccine for hepatitis B. Dev Biol (Basel). 2000;104:115-9.*

(Continued)

*Primary Examiner* — Benjamin P Blumel  
*Assistant Examiner* — Rachel Gill  
(74) *Attorney, Agent, or Firm* — Austin W. Zhang

(57) ABSTRACT

A nucleic acid construct comprising a chimeric promoter sequence and a cloning site for insertion of a coding sequence in operable linkage with the chimeric promoter, wherein the chimeric promoter sequence comprises: (a) a hCMV immediate early promoter sequence; (b) exon 1 and at least a part of exon 2 of the hCMV major immediate early gene; and (c) a heterologous intron provided in place of the intron A region of the hCMV major immediate early gene.

25 Claims, 13 Drawing Sheets

(56) References Cited

OTHER PUBLICATIONS

Arrington et al., "Plasmid Vectors Encoding Cholera Toxin or the Heat-Labile Enterotoxin from *Escherichia coli* Are Strong Adjuvants for DNA Vaccines," *Journal of Virology*, May 2002, pp. 4536-4546, vol. 76, No. 9, [XP-002379962].

Banerji et al., "Expression of a β-Globin Gene Is Enhanced by Remote SV40 DNA Sequences," *Cell*, Dec. 1981 (Part 1), pp. 299-208, vol. 27.

Bardiya et al., "Influenza Vaccines: Recent Advances in Production Technologies," *Appl Microbiol Biotechnol*, 2005, pp. 299-305, vol. 67, No. 3 [XP-002379964].

Chan et al., "Synergistic Interactions between Overlapping Binding Sites for the Serum Response Factor and ELK-1 Proteins Mediate both Basal Enhancement and Phorbol Ester Responsiveness of Primate Cytomegalovirus Major Immediate-Early Promoters in Monocyte and T-Lymphocyte Cell Types," *Journal of Virology*, Dec. 1996, pp. 8590-8605, vol. 70, No. 12 [XP-002331463].

Chapman et al., "Effect of Intron A from Human Cytomegalovirus (Towne) Immediate-Early Gene on Heterologous Expression in Mammalian Cells," *Nucleic Acids Research*, 1991, pp. 3979-3986. vol. 19, No. 14, Oxford University Press.

deVilliers et al., "A Small Segment of Polyoma Virus DNA Enhanes the Expression of a Cloned β-Globin Gene over a Distance of 1400 Base Pairs," *Nucleic Acids Research*, 1981, pp. 6251-6264, vol. 9, No. 23.

Donnelly et al., "Preclinical Efficacy of a Prototype DNA Vaccine: Enhanced Protection Against Antigenic Drift in Influenza Virus," *Nature Medicine*, Jun. 1995, pp. 583-587, vol. 1, No. 6 [XP 000508527].

Fuller et al., "Immune Responses to Hepatitis B Virus Surface and Core Antigens in Mice, Monkeys, and Pigs after Accell® Particle-Mediated DNA Immunization," *Annals New York Academy of Sciences*,1995, pp. 282-284, vol. 772, No. 27 [XP-000891484].

Garmory et al., "DNA Vaccines: Improving Expression of Antigens," *Genetic Vaccines and Therapy*, 2003, pp. 1-5, vol. 1, No. 2 [XP-002379963].

Haensler et al., "Intradermal DNA Immunization by Using Jet-Injections in Mice and Monkeys," *Vaccine*, 1999, pp. 628-638, vol. 17, Nos. 7-8.

Hearing et al., "The Adenovirus Type 5 E1A Transcriptional Control Region Contains a Duplicated Enhancer Element," *Cell*, Jul. 1983, pp. 695-703, vol. 33.

Kutinova et al., "Hepatitis B virus proteins expressed by recombinant vaccinia viruses: influence of preS2 sequence on expression surface and nucleocapsid proteins in human diploid cells," *Archives of Virology*, 1994, pp. 1-15, vol. 134.

Lee et al., "Development of a Polynucleotide Vaccine from Melanoma Antigen Recognized by T Cells-1 and Recombinant Protein from Melanoma Antigen Recognized by T Cells-1 for Melanoma Vaccine Clinical Trials," *Journal of Immunotherapy*, 2000, pp. 379-386, vol. 23, No. 3.

Levinson et al., "Activation of SV40 genome by 72-base pair tandem repeats of Moloney sarcoma virus," *Nature*, Feb. 1982, pp. 568-5721, vol. 295.

Löser et al., "Evaluation of HBV Promoters for Use in Hepatic Gene Therapy," *Biol Chem.*, Mar. 1996, pp. 187-193, vol. 377.

Luciw et al., "Location and Function of Retroviral and SV40 Sequences That Enchance Biochemical Transformation after Microinjection of DNA," *Cell*, Jul. 1983, pp. 705-716, vol. 33.

Masuda et al., "Effect of the PreS1 RNA Sequence on the Efficiency of the Hepatitis B Virus PreS2 and S Protein Translation," *Virology*, pp. 320-324, vol. 174.

Montgomery et al., "Heterologous and Homologous Protection Against Influenza A by DNA Vaccination: Optimization of DNA Vectors," *DNA and Cell Biology*, 1993, pp. 777-783, vol. 12, No. 9 [XP 000565708].

Rosenthal et al., "BK Viral Enhancer Element and a Human Cellular Homolog," *Science*, 1983, pp. 749-755, vol. 222.

Rotondaro et al., "Efficiency of different viral promoters in directing gene expression in mammalian cells: effect of 3'—untranslated sequences," *Gene*, 1996, pp. 195-198, vol. 168, No. 2.

Roy et al., "Induction of antigen-specific CD8 + T cells, T helper cells, and protective levels of antibody in humans by particle-mediated administration of a hepatitis B virus DNA vaccine," *Vaccine*, 2001, pp. 764-778, vol. 19.

Simari et al., "Improved transgene expression in vascular smooth muscle cells using downstream sequences from the CMV IE gene," *Circulation*, Supplement 1, Oct. 15, 1996, p. 1-44, vol. 94, No. 8.

Simonsen et al., "Analysis of Processing and Polyadenylation Signals of the Hepatitis B Virus Surface Antigen Gene by Using Simian Virus 40-Hepatitis B Virus Chimeric Plasmids," *Molecular and Cellular Biology*, Dec. 1983, pp. 2250-2258, vol. 3, No. 12.

Wasenauer et al., "A Cysteine and a Hydrophobic Sequence in the Noncleaved Portion of the Pre-C Leader Peptide Determine the Biophysical Properties of the Secretary Core Protein (HBe Protein) of Human hepatitis B Virus," *Journal of Virology*, Sep. 1992, pp. 5338-5346, vol. 66, No. 9 [XP-002977293].

Weeks et al., "E1A Control of Gene Expression Is Mediated by Sequences 5' to the Transcriptional Starts of the Early Viral Genes," *Molecular and Cellular Biology*, Jul. 1983, pp. 1222-1234, vol. 3.

Yang et al., "Particle Bombardment Technology for Gene Transfer (1994)," Oxford University Press, New York, NY, 1994, pp. 10-11.

Zinckgraf et al., "Modulating gene expression using DNA vaccines with different 3'-UTRs influences antibody titer, seroconversion and cytokine profiles," *Vaccine*, 2003, pp. 1640-1649, vol. 21, No. 15.

Roy et al., "Induction of antigen-specific CD8+ T cells, T helper cells, and protective levels of antibody in humans by particle-mediated administration of a hepatitis B virus DNA vaccine," *Vaccine*, vol. 19, No. 7-8, Nov. 22, 2000, pp. 764-778, XP004225394.

Zinckgraf et al., "Modulating gene expression using DNA vaccines with different 3'-UTRs influences antibody titer, seroconversion and cytokine profiles," *Vaccine*, vol. 21, No. 15, Apr. 2, 2003, pp. 1640-1649, XP004413571.

Rotondaro et al., "Efficiency of different viral promoters in directing gene expression in mammalian cells: effect of 3@?-untranslated sequences," Gene, vol. 168, No. 2, Feb. 12, 1996, pp. 195-198, XP004042959.

Chan et al., "Synergistic interactions between overlapping binding sites for the serum response factor and ELK-1 proteins mediate both basal enhancement and phorbol ester responsiveness of primate cytomegalovirus major immediate-early promoters in monocyte and T-lymphocyte cell types," *Journal of Virology*, vol . 70, No. 12, 1996, pp. 8590-8605, XP002331463.

Fuller et al: "Immune Responses to Hepatitis B Virus Surface and Core Antigens in Mice Monkeys and Pigs After Accell Particle-Mediated Dan Immunization, " *Annals of the New York Academy of Sciences*, vol. 772, Nov. 27, 1995, pp. 282-284, XP000891484.

Wasenauer et al., "A Cysteine and a Hydrophobic Sequence in the Noncleaved Portion o f the Pre-C leader peptide Determine the Biophysical Properties of the Secretory Core Protein (HBe protein) of Human Hepatitis B Virus," *Journal of Virology*, vol . 66, No. 9, Sep. 1992, pp. 5338-5346, XP002977293.

\* cited by examiner

Figure 13 ggcgtaatgctctgccagtgttacaaccaattaaccaattctgattagaaaaactcatcgagcatcaaatgaaactgcaatttattcatat
caggattatcaataccatattttgaaaaagccgtttctgtaatgaaggagaaaactcaccgaggcagttccataggatggcaagatcc
tggtatcggtctgcgattccgactcgtccaacatcaatacaacctattaatttccctcgtcaaaaataaggttatcaagtgagaaatca
ccatgagtgacgactgaatccggtgagaatggcaaaagcttatgcatttctttccagacttgttcaacaggccagccattacgctcgtc
atcaaaatcactcgcatcaaccaaaccgttattcattcgtgattgcgcctgagcgagacgaaatacgcgatcgctgttaaaaggacaa
ttacaaacaggaatcgaatgcaaccggcgcaggaacactgccagcgcatcaacaatattttcacctgaatcaggatattcttctaata
cctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctgg
cgcatcgggcttcccatacaatcgatagattgtcgcacctgattgcccgacattatcgcgagcccatttatacccatataaatcagcat
ccatgttggaatttaatcgcggcctcgagcaagacgtttcccgttgaatatggctcataacaccccttgtattactgtttatgtaagcaga
caggtcgacaatattggctattggccattgcatacgttgtatctatatcataatatgtacatttatattggctcatgtccaatatgaccgcca
tgttgacattgattattgactagttattaatagtaatcaattacggggtcattagttcatagcccatatatggagttccgcgttacataactta
cggtaaatggcccgcctggctgaccgcccaacgacccccgcccattgacgtcaataatgacgtatgttcccatagtaacgccaata
gggactttccattgacgtcaatgggtggagtatttacggtaaactgcccacttggcagtacatcaagtgtatcatatgccaagtccgcc
ccctattgacgtcaatgacggtaaatggcccgcctggcattatgcccagtacatgaccttacgggactttcctacttggcagtacatct
acgtattagtcatcgctattaccatggtgatgcggttttggcagtacaccaatgggcgtggatagcggtttgactcacggggatttcca
agtctccacccattgacgtcaatgggagtttgttttggcaccaaaatcaacgggactttccaaaatgtcgtaataacccccgccccgtt
gacgcaaatgggcggtaggcgtgtacggtgggaggtctatataagcagagctcgtttagtgaaccgtcagatcgcctggagacgc
catccacgctgttttgacctccatagaagacaccgggaccgatccagcctccgcggccgggaacggtgcattggaacgcggattc
cccgtgccaagagtgactcaccgtccggatctcagcaagcaggtatgtactctccagggtgggcctggcttccccagtcaagactc
cagggatttgagggacgctgtgggctcttctcttacatgtacctttgcttgcctcaaccctgactatcttccaggtcaggatcccagag
tcaggggtctgtattttcctgctggtggctccagttcaggaacagtaaaccctgctccgaatattgcctctcacatctcgtcaatctccg
cgaggactggggaccctgtgacgaacatggctagcgggcccagatctgggccctaacaaaacaaaaagatgggggttattccctaa
acttcatgggttacgtaattggaagttgggggacattgccacaagatcatattgtacaaaagatcaaacactgttttagaaaacttcctg
taaacaggcctattgattggaaagtatgtcaaaggattgtgggtcttttgggcttgtgctgctccatttacacaatgtggatatcctgcctta
atgcctttgtatgcatgtatacaagctaaacaggcttcactttctcgccaacttacaaggcctttctaagtaaacagtacatgaacccttta
ccccgttgctcggcaacgcctggtctgtgccaagtgtttgctgacgcaaccccactggctggggcttggccataggccatcagc
gcatgcgtggaaccttgtggctcctctgccgatccatactgcggaactcctagccgcttgttttgctcgcagccggtctggagcaaa
gctcataggaactgacaattctgtcgtcctctcgcgaaatatacatcgtttcgatctacgtatgatcttttcccctctgccaaaaattatg
gggacatcatgaagccccttgagcatctgacttctggctaataaaggaaatttatttttcattgcaatagtgtgttggaatttttttgtgtctct
cactcggaaggaattctgcattaatgaatcggccaacgcgcggggagaggcggtttgcgtattgggcgctcttccgcttcctcgctc
actgactcgctgcgctcggtcgttcggctgcggcgagcggtatcagctcactcaaaggcggtaatacggttatccacagaatcagg
ggataacgcaggaaagaacatgtgagcaaaaggccagcaaaaggccaggaaccgtaaaaaggccgcgttgctggcgtttttcca
taggctccgcccccctgacgagcatcacaaaaatcgacgctcaagtcagaggtggcgaaacccgacaggactataaagatacca
ggcgtttccccctggaagctccctcgtgcgctctcctgttccgaccctgccgcttaccggatacctgtccgcctttctcccttcgggaa
gcgtggcgctttctcatagctcacgctgtaggtatctcagttcggtgtaggtcgttcgctccaagctgggctgtgtgcacgaaccccc
cgttcagcccgaccgctgcgccttatccggtaactatcgtcttgagtccaacccggtaagacacgacttatcgccactggcagcagc
cactggtaacaggattagcagagcgaggtatgtaggcggtgctacagagttcttgaagtggtggcctaactacggctacactagaa
gaacagtatttggtatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgatcttttctacggggtct
gacgctcagtggaacgaaaactcacgttaagggattttggtcatgagattatcaaaaaggatcttcacctagatcctttaaattaaaaa
tgaagttttaaatcaatctaaagtatatatgagtaaacttggtctgacagttaccaatgcttaatcagtgaggcacctatctcagcgatct
gtctatttcgttcatccatagttgcctgactc

SEQUENCE LISTING

```
<160> NUMBER OF SEQ ID NOS: 54

<210> SEQ ID NO 1
<211> LENGTH: 685
<212> TYPE: DNA
<213> ORGANISM: Human cytomegalovirus

<400> SEQUENCE: 1
aatattggct attggccatt gcatacgttg tatctatatc ataatatgta catttatatt      60
ggctcatgtc caatatgacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gaccccccgcc cattgacgtc aataatgacg     240
tatgttccca tagtaacgcc aatagggact ttccattgac gtcaatgggt ggagtattta     300
cggtaaactg cccacttggc agtacatcaa gtgtatcata tgccaagtcc gccccctatt     360
gacgtcaatg acggtaaatg gcccgcctgg cattatgccc agtacatgac cttacgggac     420
tttcctactt ggcagtacat ctacgtatta gtcatcgcta ttaccatggt gatgcggttt     480
tggcagtaca ccaatgggcg tggatagcgg tttgactcac ggggatttcc aagtctccac     540
cccattgacg tcaatgggag tttgttttgg caccaaaatc aacgggactt tccaaaatgt     600
cgtaataacc ccgccccgtt gacgcaaatg ggcggtaggc gtgtacggtg ggaggtctat     660
ataagcagag ctcgtttagt gaacc                                            685

<210> SEQ ID NO 2
<211> LENGTH: 131
<212> TYPE: DNA
<213> ORGANISM: Human cytomegalovirus

<400> SEQUENCE: 2
gtcagatcgc ctggagacgc catccacgct gttttgacct ccatagaaga caccgggacc      60
gatccagcct ccgcggccgg gaacggtgca ttggaacgcg gattccccgt gccaagagtg     120
actcaccgtc c                                                           131

<210> SEQ ID NO 3
<211> LENGTH: 135
```

```
<212> TYPE: DNA
<213> ORGANISM: Rattus rattus

<400> SEQUENCE: 3
atcagcaagc aggtatgtac tctccagggt gggcctggct tccccagtca agactccagg      60
gatttgaggg acgctgtggg ctcttctctt acatgtacct tttgctagcc tcaaccctga     120
ctatcttcca ggtca                                                      135

<210> SEQ ID NO 4
<211> LENGTH: 955
<212> TYPE: DNA
<213> ORGANISM: Artificial sequence
<220> FEATURE:
<223> OTHER INFORMATION: Description of Artificial Sequence: Synthetic
      chimeric promoter sequence

<400> SEQUENCE: 4
aatattggct attggccatt gcatacgttg tatctatatc ataatatgta catttatatt      60
ggctcatgtc caatatgacc gccatgttga cattgattat tgactagtta ttaatagtaa    120
tcaattacgg ggtcattagt tcatagccca tatatggagt ccgcgttac ataacttacg     180 gtaaatggcc cgcctggctg accgcccaac gacccccgcc cattgacgtc aataatgacg    240
tatgttccca tagtaacgcc aatagggact ttccattgac gtcaatgggt ggagtattta    300
cggtaaactg cccacttggc agtacatcaa gtgtatcata tgccaagtcc gccccctatt    360
gacgtcaatg acggtaaatg gcccgcctgg cattatgccc agtacatgac cttacgggac    420
tttcctactt ggcagtacat ctacgtatta gtcatcgcta ttaccatggt gatgcggttt    480
tggcagtaca ccaatgggcg tggatagcgg tttgactcac ggggatttcc aagtctccac    540
cccattgacg tcaatgggag tttgttttgg caccaaaatc aacgggactt tccaaaatgt    600
cgtaataacc ccgcccgtt gacgcaaatg ggcggtaggc gtgtacggtg ggaggtctat    660
ataagcagag ctcgtttagt gaaccgtcag atcgcctgga gacgccatcc acgctgtttt    720
gacctccata gaagacaccg ggaccgatcc agcctccgcg gccgggaacg gtgcattgga    780
acgcggattc cccgtgccaa gagtgactca ccgtccggat ctcagcaagc aggtatgtac    840
tctccagggt gggcctggct tccccagtca agactccagg gatttgaggg acgctgtggg    900
ctcttctctt acatgtacct tttgcttgcc tcaaccctga ctatcttcca ggtca          955

<210> SEQ ID NO 5
<211> LENGTH: 121
<212> TYPE: DNA
<213> ORGANISM: Hepatitis B virus

<400> SEQUENCE: 5
cagagtcagg ggtctgtatt ttcctgctgg tggctccagt tcaggaacag taaaccctgc      60
tccgaatatt gcctctcaca tctcgtcaat ctccgcgagg actggggacc ctgtgacgaa     120
c                                                                     121

<210> SEQ ID NO 6
<211> LENGTH: 57
<212> TYPE: DNA
<213> ORGANISM: Herpes simplex virus

<400> SEQUENCE: 6
ataagctgca ttgcgaacca ctagtcgccg ttttcgtgt gcatcgcgta tcacggc           57

<210> SEQ ID NO 7
```

```
<211> LENGTH: 48
<212> TYPE: DNA
<213> ORGANISM: Hepatitis B virus

<400> SEQUENCE: 7
ctttgtacta ggaggctgta ggcataaatt ggtctgttca ccagcacc            48

<210> SEQ ID NO 8
<211> LENGTH: 533
<212> TYPE: DNA
<213> ORGANISM: Hepatitis B virus

<400> SEQUENCE: 8
taacaaaaca aaaagatggg gttattccct aaacttcatg ggttacgtaa ttggaagttg    60
ggggacattg ccacaagatc atattgtaca aaagatcaaa cactgtttta gaaaacttcc   120
tgtaaacagg cctattgatt ggaaagtatg tcaaaggatt gtgggtcttt gggctttgc    180 tgctccattt acacaatgtg gatatcctgc cttaatgcct ttgtatgcat gtatacaagc   240
taaacaggct ttcactttct cgccaactta caaggccttt ctaagtaaac agtacatgaa   300
cctttacccc gttgctcggc aacggcctgg tctgtgccaa gtgtttgctg acgcaacccc   360
cactggctgg ggcttggcca taggccatca gcgcatgcgt ggaacctttg tggctcctct   420
gccgatccat actgcggaac tcctagccgc ttgttttgct cgcagccggt ctggagcaaa   480
gctcatagga actgacaatt ctgtcgtcct ctcgcggaaa tatacatcgt ttc          533

<210> SEQ ID NO 9
<211> LENGTH: 158
<212> TYPE: DNA
<213> ORGANISM: Simian cytomegalovirus

<400> SEQUENCE: 9
gtcagacaga cagacagtta tatgggctgg tccctataac tctgccattg taaccccata    60
tagccagaca gttagcattg catctattga tgatgtacta atgtattgta acccccccta   120
tgccattgtc taactgtact aatgtatgat attatacc                           158

<210> SEQ ID NO 10
<211> LENGTH: 131
<212> TYPE: DNA
<213> ORGANISM: Oryctolagus cuniculus

<400> SEQUENCE: 10 gatcttttc cctctgccaa aaattatggg gacatcatga agcccttga gcatctgact      60 tctggctaat aaaggaaatt tattttcatt gcaatagtgt gttggaattt tttgtgtctc   120
tcactcggaa g                                                        131

<210> SEQ ID NO 11
<211> LENGTH: 204
<212> TYPE: DNA
<213> ORGANISM: Simian cytomegalovirus

<400> SEQUENCE: 11
atatatactc tatgttatac tctatgatat acaatatata ctcatgaaca ctatgtactt    60
ggtgtatgac tcattattgt ctgggacttg gttgggactt ggttggttgg gaagaatgtt   120
gtgcctgtac ttgtgctgtg ctgtggatct caataaatgt gactatgttc aaaacactaa   180
gtgcccccgt gtcttcttta acta                                          204

<210> SEQ ID NO 12
```

```
<211> LENGTH: 163
<212> TYPE: DNA
<213> ORGANISM: Herpes simplex virus 2

<400> SEQUENCE: 12
gaagacgagc tctaagggag gggaggggag ctgggcttgt gtataaataa aaagacaccg      60
atgttcaaaa atacacatga cttctggtat tgttttgcct tggttttat ttggggggg      120 gggggcgtgt gactagaaaa acaaatgcag acatgtgcta acg                       163

<210> SEQ ID NO 13
<211> LENGTH: 191
<212> TYPE: DNA
<213> ORGANISM: Human papillomavirus type 16

<400> SEQUENCE: 13
aattgttaca tataattgtt gtataccata acttactatt ttttcttttt tattttcata      60 tataatttt tttttgttt gtttgtttgt tttttaataa actgttatta cttaacaatg      120
cgacacaaac gttctgcaaa acgcacaaaa cgtgcatcgg ctacccaact ttataaaaca      180
tgcaaacagg c                                                           191

<210> SEQ ID NO 14
<211> LENGTH: 3759
<212> TYPE: DNA
<213> ORGANISM: Artificial sequence
<220> FEATURE:
<223> OTHER INFORMATION: Description of Artificial Sequence: Synthetic
      pJV expression vector
<220> FEATURE:
<221> NAME/KEY: Intron
<222> LOCATION: (1725)..(1857)
<223> OTHER INFORMATION: Rat Ins IntA
<220> FEATURE:
<221> NAME/KEY: misc_feature
<222> LOCATION: (1)..(44)
<223> OTHER INFORMATION: Tn903, pUC4K Remnants
<220> FEATURE:
<221> NAME/KEY: misc_feature
<222> LOCATION: (861)..(896)
<223> OTHER INFORMATION: Tn903, pUC4K Remnants
<220> FEATURE:
<221> NAME/KEY: misc_feature
<222> LOCATION: (897)..(902)
<223> OTHER INFORMATION: pUC19 MCS
<220> FEATURE:
<221> NAME/KEY: polyA_signal
<222> LOCATION: (2556)..(2686)
<223> OTHER INFORMATION: rGLOB pA
<220> FEATURE:
<221> NAME/KEY: polyA_site
<222> LOCATION: (2647)..(2647)
<223> OTHER INFORMATION: PolyA_Site_1
<220> FEATURE:
<221> NAME/KEY: promoter
<222> LOCATION: (903)..(1587)
<223> OTHER INFORMATION: CMV Pro
<220> FEATURE:
<221> NAME/KEY: 3'UTR
<222> LOCATION: (2012)..(2544)
<223> OTHER INFORMATION: HBVenh
<220> FEATURE:
<221> NAME/KEY: 5'UTR
<222> LOCATION: (1864)..(1984)
<223> OTHER INFORMATION: 5'-UTR of HBV pre-S2
<220> FEATURE:
<221> NAME/KEY: misc_feature
<222> LOCATION: (1719)..(1724)
<223> OTHER INFORMATION: Bam/Bgl fusion
<220> FEATURE:
<221> NAME/KEY: misc_feature
<222> LOCATION: (1985)..(1987)
<223> OTHER INFORMATION: ATG-Nhe
```

```
<220> FEATURE:
<221> NAME/KEY: misc_feature
<222> LOCATION: (1988)..(2011)
<223> OTHER INFORMATION: CDS insertion site
<220> FEATURE:
<221> NAME/KEY: misc_feature
<222> LOCATION: (2545)..(2555)
<223> OTHER INFORMATION: unknown
<220> FEATURE:
<221> NAME/KEY: exon
<222> LOCATION: (1588)..(1718)
<223> OTHER INFORMATION: CMV Exon 1/2
<220> FEATURE:
<221> NAME/KEY: misc_feature
<222> LOCATION: (2693)..(3759)
<223> OTHER INFORMATION: pUC19
<220> FEATURE:
<221> NAME/KEY: misc_feature
<222> LOCATION: (45)..(860)
<223> OTHER INFORMATION: KanR (Tn903) complement

<400> SEQUENCE: 14
ggcgtaatgc tctgccagtg ttacaaccaa ttaaccaatt ctgattagaa aaactcatcg      60
agcatcaaat gaaactgcaa tttattcata tcaggattat caataccata ttttgaaaa     120 agccgtttct gtaatgaagg agaaaactca ccgaggcagt tccataggat ggcaagatcc    180
tggtatcggt ctgcgattcc gactcgtcca acatcaatac aacctattaa tttccctcg    240 tcaaaaataa ggttatcaag tgagaaatca ccatgagtga cgactgaatc cggtgagaat    300
ggcaaaagct tatgcatttc tttccagact tgttcaacag gccagccatt acgctcgtca    360
tcaaaatcac tcgcatcaac caaaccgtta ttcattcgtg attgcgcctg agcgagacga    420
aatacgcgat cgctgttaaa aggacaatta caaacaggaa tcgaatgcaa ccggcgcagg    480
aacactgcca gcgcatcaac aatattttca cctgaatcag gatattcttc taatacctgg    540
aatgctgttt tcccggggat cgcagtggtg agtaaccatg catcatcagg agtacggata    600
aaatgcttga tggtcggaag aggcataaat tccgtcagcc agtttagtct gaccatctca    660
tctgtaacat cattggcaac gctacctttg ccatgtttca gaaacaactc tggcgcatcg    720
ggcttcccat acaatcgata gattgtcgca cctgattgcc cgacattatc gcgagcccat    780
ttatacccat ataaatcagc atccatgttg gaatttaatc gcggcctcga gcaagacgtt    840
tcccgttgaa tatggctcat aacacccctt gtattactgt ttatgtaagc agacaggtcg    900
acaatattgg ctattggcca ttgcatacgt tgtatctata tcataatatg tacatttata    960
ttggctcatg tccaatatga ccgccatgtt gacattgatt attgactagt tattaatagt   1020
aatcaattac ggggtcatta gttcatagcc catatatgga gttccgcgtt acataactta   1080
cggtaaatgg cccgcctggc tgaccgccca acgacccccg cccattgacg tcaataatga   1140
cgtatgttcc catagtaacg ccaataggga ctttccattg acgtcaatgg gtggagtatt   1200
tacggtaaac tgcccacttg gcagtacatc aagtgtatca tatgccaagt ccgccccta    1260 ttgacgtcaa tgacggtaaa tggcccgcct ggcattatgc ccagtacatg accttacggg   1320
actttcctac ttggcagtac atctacgtat tagtcatcgc tattaccatg gtgatgcggt   1380
tttggcagta caccaatggg cgtggatagc ggtttgactc acggggattt ccaagtctcc   1440
accccattga cgtcaatggg agtttgtttt ggcaccaaaa tcaacgggac tttccaaaat   1500
gtcgtaataa ccccgcccg ttgacgcaaa tgggcggtag cgtgtacgg tgggaggtct    1560 atataagcag agctcgttta gtgaacc gtc aga tcg cct gga gac gcc atc cac   1614
                                   Val Arg Ser Pro Gly Asp Ala Ile His
                                    1               5 gct gtt ttg acc tcc ata gaa gac acc ggg acc gat cca gcc tcc gcg       1662
```

```
Ala Val Leu Thr Ser Ile Glu Asp Thr Gly Thr Asp Pro Ala Ser Ala
 10              15                  20                  25 gcc ggg aac ggt gca ttg gaa cgc gga ttc ccc gtg cca aga gtg act      1710
Ala Gly Asn Gly Ala Leu Glu Arg Gly Phe Pro Val Pro Arg Val Thr
             30                  35                  40 cac cgt cc ggatctcagc aagcaggtat gtactctcca gggtgggcct ggcttcccca    1768
His Arg gtcaagactc cagggatttg agggacgctg tgggctcttc tcttacatgt acctttgct     1828 tgcctcaacc ctgactatct tccaggtcag gatcccagag tcaggggtct gtattttcct    1888
gctggtggct ccagttcagg aacagtaaac cctgctccga atattgcctc tcacatctcg    1948
tcaatctccg cgaggactgg ggaccctgtg acgaacatgg ctagcgggcc cagatctggg    2008
ccctaacaaa acaaaaagat ggggttattc cctaaacttc atgggttacg taattggaag    2068
ttgggggaca ttgccacaag atcatattgt acaaaagatc aaacactgtt ttagaaaact    2128
tcctgtaaac aggcctattg attggaaagt atgtcaaagg attgtgggtc ttttgggctt    2188
tgctgctcca tttacacaat gtggatatcc tgccttaatg cctttgtatg catgtataca    2248
agctaaacag gctttcactt tctcgccaac ttacaaggcc tttctaagta acagtacat     2308 gaacctttac cccgttgctc ggcaacggcc tggtctgtgc caagtgtttg ctgacgcaac    2368
ccccactggc tggggcttgg ccataggcca tcagcgcatg cgtggaacct tgtggctcc     2428 tctgccgatc catactgcgg aactcctagc cgcttgtttt gctcgcagcc ggtctggagc    2488
aaagctcata ggaactgaca attctgtcgt cctctcgcgg aaatatacat cgtttcgatc    2548
tacgtatgat cttttttccct ctgccaaaaa ttatggggac atcatgaagc cccttgagca   2608
tctgacttct ggctaataaa ggaaatttat tttcattgca atagtgtgtt ggaattttt     2668 gtgtctctca ctcggaagga attctgcatt aatgaatcgg ccaacgcgcg gggagaggcg    2728
gtttgcgtat tgggcgctct tccgcttcct cgctcactga ctcgctgcgc tcggtcgttc    2788
ggctgcggcg agcggtatca gctcactcaa aggcggtaat acggttatcc acagaatcag    2848
gggataacgc aggaaagaac atgtgagcaa aaggccagca aaaggccagg aaccgtaaaa    2908
aggccgcgtt gctggcgttt ttccataggc tccgcccccc tgacgagcat cacaaaaatc    2968
gacgctcaag tcagaggtgg cgaaacccga caggactata agataccag gcgtttcccc     3028 ctggaagctc cctcgtgcgc tctcctgttc gaccctgcc gcttaccgga tacctgtccg     3088
cctttctccc ttcgggaagc gtggcgcttt ctcatagctc acgctgtagg tatctcagtt    3148
cggtgtaggt cgttcgctcc aagctgggct gtgtgcacga accccccgtt cagcccgacc    3208
gctgcgcctt atccggtaac tatcgtcttg agtccaaccc ggtaagacac gacttatcgc    3268
cactggcagc agccactggt aacaggatta gcagagcgag gtatgtaggc ggtgctacag    3328
agttcttgaa gtggtggcct aactacggct acactagaag aacagtattt ggtatctgcg    3388
ctctgctgaa gccagttacc ttcggaaaaa gagttggtag ctcttgatcc ggcaaacaaa    3448
ccaccgctgg tagcggtggt ttttttgttt gcaagcagca gattacgcgc agaaaaaaag    3508
gatctcaaga agatccttg atcttttcta cggggtctga cgctcagtgg aacgaaaact     3568
cacgttaagg gattttggtc atgagattat caaaaaggat cttcacctag atccttttaa    3628
attaaaaatg aagttttaaa tcaatctaaa gtatatatga gtaaacttgg tctgacagtt    3688
accaatgctt aatcagtgag gcacctatct cagcgatctg tctatttcgt tcatccatag    3748
ttgcctgact c                                                         3759

<210> SEQ ID NO 15
```

```
<211> LENGTH: 42
<212> TYPE: DNA
<213> ORGANISM: Artificial sequence
<220> FEATURE:
<223> OTHER INFORMATION: Description of Artificial Sequence: Synthetic
      primer

<400> SEQUENCE: 15
ggaggatccg gacggtgagt cactcttggc acggggaatc cg                        42

<210> SEQ ID NO 16
<211> LENGTH: 21
<212> TYPE: DNA
<213> ORGANISM: Artificial sequence
<220> FEATURE:
<223> OTHER INFORMATION: Description of Artificial Sequence: Synthetic
      primer

<400> SEQUENCE: 16
ggtgaatatg gctcataaca c                                               21

<210> SEQ ID NO 17
<211> LENGTH: 23
<212> TYPE: DNA
<213> ORGANISM: Artificial sequence
<220> FEATURE:
<223> OTHER INFORMATION: Description of Artificial Sequence: Synthetic
      primer

<400> SEQUENCE: 17
ccgccgaaca tggagaacat cgc                                             23

<210> SEQ ID NO 18
<211> LENGTH: 33
<212> TYPE: DNA
<213> ORGANISM: Artificial sequence
<220> FEATURE:
<223> OTHER INFORMATION: Description of Artificial Sequence: Synthetic
      primer

<400> SEQUENCE: 18
cacagatctt ttgttagggt ttaaatgtat acc                                  33

<210> SEQ ID NO 19
<211> LENGTH: 29
<212> TYPE: DNA
<213> ORGANISM: Artificial sequence
<220> FEATURE:
<223> OTHER INFORMATION: Description of Artificial Sequence: Synthetic
      primer

<400> SEQUENCE: 19
ggaggatcct gacctggaag atagtcacc                                       29

<210> SEQ ID NO 20
<211> LENGTH: 26
<212> TYPE: DNA
<213> ORGANISM: Artificial sequence
<220> FEATURE:
<223> OTHER INFORMATION: Description of Artificial Sequence: Synthetic
      primer

<400> SEQUENCE: 20
ggaggatcca tcagcaagca ggtatg                                          26

<210> SEQ ID NO 21
<211> LENGTH: 33
<212> TYPE: DNA
```

```
<213> ORGANISM: Artificial sequence
<220> FEATURE:
<223> OTHER INFORMATION: Description of Artificial Sequence: Synthetic
      primer

<400> SEQUENCE: 21
ggagctagcg ggcgtttgac ctccggcgtc ggg                                    33

<210> SEQ ID NO 22
<211> LENGTH: 37
<212> TYPE: DNA
<213> ORGANISM: Artificial sequence
<220> FEATURE:
<223> OTHER INFORMATION: Description of Artificial Sequence: Synthetic
      primer

<400> SEQUENCE: 22
ggagaattca gatctcctct agtaaaacaa tggctgg                                37

<210> SEQ ID NO 23
<211> LENGTH: 25
<212> TYPE: DNA
<213> ORGANISM: Artificial sequence
<220> FEATURE:
<223> OTHER INFORMATION: Description of Artificial Sequence: Synthetic
      primer

<400> SEQUENCE: 23
ggagctagcc ttctaaccga ggtcg                                             25

<210> SEQ ID NO 24
<211> LENGTH: 30
<212> TYPE: DNA
<213> ORGANISM: Artificial sequence
<220> FEATURE:
<223> OTHER INFORMATION: Description of Artificial Sequence: Synthetic
      primer

<400> SEQUENCE: 24
ggaagatctc cttactccag ctctatgctg                                        30

<210> SEQ ID NO 25
<211> LENGTH: 27
<212> TYPE: DNA
<213> ORGANISM: Artificial sequence
<220> FEATURE:
<223> OTHER INFORMATION: Description of Artificial Sequence: Synthetic
      primer

<400> SEQUENCE: 25
ggcgaattcc ttccgagtga gagacac                                           27

<210> SEQ ID NO 26
<211> LENGTH: 43
<212> TYPE: DNA
<213> ORGANISM: Artificial sequence
<220> FEATURE:
<223> OTHER INFORMATION: Description of Artificial Sequence: Synthetic
      primer

<400> SEQUENCE: 26
ggagtataca tttaaagggc cctaacaaaa caaaaagatg ggg                         43

<210> SEQ ID NO 27
<211> LENGTH: 31
<212> TYPE: DNA
<213> ORGANISM: Artificial sequence
<220> FEATURE:
```

<223> OTHER INFORMATION: Description of Artificial Sequence: Synthetic
      primer

<400> SEQUENCE: 27
ggagctagct cgtttacttt gaccaagaac g                                    31

<210> SEQ ID NO 28
<211> LENGTH: 36
<212> TYPE: DNA
<213> ORGANISM: Artificial sequence
<220> FEATURE:
<223> OTHER INFORMATION: Description of Artificial Sequence: Synthetic
      primer

<400> SEQUENCE: 28
ggaagatctc cttatttttg acaccagacc aactgg                               36

<210> SEQ ID NO 29
<211> LENGTH: 29
<212> TYPE: DNA
<213> ORGANISM: Artificial sequence
<220> FEATURE:
<223> OTHER INFORMATION: Description of Artificial Sequence: Synthetic
      primer

<400> SEQUENCE: 29
ggagtcgacc tgtctgctta cataaacag                                       29

<210> SEQ ID NO 30
<211> LENGTH: 26
<212> TYPE: DNA
<213> ORGANISM: Artificial sequence
<220> FEATURE:
<223> OTHER INFORMATION: Description of Artificial Sequence: Synthetic
      primer

<400> SEQUENCE: 30
cgtaatgctc tgccagtgtt acaacc                                          26

<210> SEQ ID NO 31
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 31
gaaagatctc agcaagcagg                                                 20

<210> SEQ ID NO 32
<211> LENGTH: 47
<212> TYPE: DNA
<213> ORGANISM: Artificial sequence
<220> FEATURE:
<223> OTHER INFORMATION: Description of Artificial Sequence: Synthetic
      primer

<400> SEQUENCE: 32
ggaggatcct gacctggaag atagtcaggg ttgaggcaag caaaagg                   47

<210> SEQ ID NO 33
<211> LENGTH: 12
<212> TYPE: DNA
<213> ORGANISM: Artificial sequence
<220> FEATURE:
<223> OTHER INFORMATION: Description of Artificial Sequence: Synthetic
      primer

```
<400> SEQUENCE: 33
ctagcgggcc ca                                                              12

<210> SEQ ID NO 34
<211> LENGTH: 12
<212> TYPE: DNA
<213> ORGANISM: Artificial sequence
<220> FEATURE:
<223> OTHER INFORMATION: Description of Artificial Sequence: Synthetic
      primer

<400> SEQUENCE: 34
gatctgggcc cg                                                              12

<210> SEQ ID NO 35
<211> LENGTH: 28
<212> TYPE: DNA
<213> ORGANISM: Artificial sequence
<220> FEATURE:
<223> OTHER INFORMATION: Description of Artificial Sequence: Synthetic
      primer

<400> SEQUENCE: 35
ggagctagca tcatcccagt tgaggagg                                             28

<210> SEQ ID NO 36
<211> LENGTH: 28
<212> TYPE: DNA
<213> ORGANISM: Artificial sequence
<220> FEATURE:
<223> OTHER INFORMATION: Description of Artificial Sequence: Synthetic
      primer

<400> SEQUENCE: 36
ggtagatctc ctcatgtctg ctcgaagc                                             28

<210> SEQ ID NO 37
<211> LENGTH: 29
<212> TYPE: DNA
<213> ORGANISM: Artificial sequence
<220> FEATURE:
<223> OTHER INFORMATION: Description of Artificial Sequence: Synthetic
      primer

<400> SEQUENCE: 37
ccaagctagc gacaaaactc acacatgcc                                            29

<210> SEQ ID NO 38
<211> LENGTH: 45
<212> TYPE: DNA
<213> ORGANISM: Artificial sequence
<220> FEATURE:
<223> OTHER INFORMATION: Description of Artificial Sequence: Synthetic
      primer

<400> SEQUENCE: 38
ggaagatctc gtttacccct gtcatttacc cggagacagg gagag                          45

<210> SEQ ID NO 39
<211> LENGTH: 57
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 39
```
aagatgtcca gactctgtct ctccgtggcc ctcctcgtgc tcctcgggac actcgcc    57

<210> SEQ ID NO 40
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 40
ggaactagta agatgtccag actc    24

<210> SEQ ID NO 41
<211> LENGTH: 25
<212> TYPE: DNA
<213> ORGANISM: Artificial sequence
<220> FEATURE:
<223> OTHER INFORMATION: Description of Artificial Sequence: Synthetic
      primer

<400> SEQUENCE: 41
ggaagctagc ggcgagtgtc ccgag    25

<210> SEQ ID NO 42
<211> LENGTH: 75
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 42
ggaaagatgg ccagcctctt tgccacattt ctcgtggtgc tcgtgagcct cagcctcgcc    60
agcgaaagca gcgcc    75

<210> SEQ ID NO 43
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 43
ggaactagtg gaaagatggc cagc    24

<210> SEQ ID NO 44
<211> LENGTH: 26
<212> TYPE: DNA
<213> ORGANISM: Artificial sequence
<220> FEATURE:
<223> OTHER INFORMATION: Description of Artificial Sequence: Synthetic
      primer

<400> SEQUENCE: 44
ggaagctagc ggcgctgctt tcgctg    26

<210> SEQ ID NO 45
<211> LENGTH: 51
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 45
aggtctttgc taatcttggt gctttgcttc ctgcccctgg ctgctctggg g    51

<210> SEQ ID NO 46
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 46
ggaactagta ggtctttgct aatc    24

<210> SEQ ID NO 47
<211> LENGTH: 25
<212> TYPE: DNA
<213> ORGANISM: Artificial sequence
<220> FEATURE:
<223> OTHER INFORMATION: Description of Artificial Sequence: Synthetic
      primer

<400> SEQUENCE: 47
ggaagctagc ccccagagca gccag    25

<210> SEQ ID NO 48
<211> LENGTH: 31
<212> TYPE: DNA
<213> ORGANISM: Artificial sequence
<220> FEATURE:
<223> OTHER INFORMATION: Description of Artificial Sequence: Synthetic
      primer

<400> SEQUENCE: 48
ggagctagct cgtttacttt gaccaagaac g    31

<210> SEQ ID NO 49
<211> LENGTH: 25
<212> TYPE: DNA
<213> ORGANISM: Artificial sequence
<220> FEATURE:
<223> OTHER INFORMATION: Description of Artificial Sequence: Synthetic
      primer

<400> SEQUENCE: 49
ggaagatctc cggtgagtgg tgctg    25

<210> SEQ ID NO 50
<211> LENGTH: 32
<212> TYPE: DNA
<213> ORGANISM: Artificial sequence
<220> FEATURE:
<223> OTHER INFORMATION: Description of Artificial Sequence: Synthetic
      primer

<400> SEQUENCE: 50
gcaggatcca gtagacctgg agagaggaca ag    32

<210> SEQ ID NO 51
<211> LENGTH: 29
<212> TYPE: DNA
<213> ORGANISM: Artificial sequence
<220> FEATURE:
<223> OTHER INFORMATION: Description of Artificial Sequence: Synthetic
      primer

<400> SEQUENCE: 51
ggaagatcta caaggtgagc tgctgtggc    29

```
<210> SEQ ID NO 52
<211> LENGTH: 490
<212> TYPE: DNA
<213> ORGANISM: Pseudo rabies virus

<400> SEQUENCE: 52
tggccgcaga gcgggccggg catgcaaatc agaggcgcgc gggagacgcc tccgcgcgcc      60
cattggcccg ggcgagccga gatggccgcc gcggggccg gacatgcaaa gtagacgcga     120
gaggaagtag ggagagaaat cccattggcc gtcgaggggc caagatggcg ccctcggggc     180
cggacatgca aagtagacgc gagaggaagt gggcgagaga atcccattg gccgtcgatg     240 gggcaagatg gccgccgcgg gggccgggca tgcaaatggt cctcgcgagg aagttcctcg     300
cgaaatccca ttggccggcg ccgccatct tgggccgggc atgcaaagca gacggcagag     360
gaagcgggcg agaaaaatcc cattggccgg ccgtcgggga agtccgcggc gaaaatcggc     420
cattggtccg cttacctggg ggcgggctct cctcggggcg cttataagcg cggtctccat     480
cgtagcactt                                                            490

<210> SEQ ID NO 53
<211> LENGTH: 495
<212> TYPE: DNA
<213> ORGANISM: Rous sarcoma virus

<400> SEQUENCE: 53
ctgctccctg cttgtgtgtt ggaggtcgct gagtagtgcg cgagcaaaat ttaagctaca      60
acaaggcaag gcttgaccga caattgcatg aagaatctgc ttagggttag gcgttttgcg     120
ctgcttcgcg atgtacgggc cagatatacg cgtatctgag gggactaggg tgtgtttagg     180
cgaaaagcgg ggcttcggtt gtacgcggtt aggagttccc tcaggatata gtagtttcgc     240
ttttgcatag ggaggggaa atgtagtctt atgcaataca cttgtagtct tgcaacatgg     300
taacgatgag ttagcaacat gccttacaag gagagaaaaa gcaccgtgca tgccgattgg     360
tggaagtaag gtggtacgat cgtgccttat taggaaggca acagacaggt ctgacatgga     420
ttggacgaac cactgaattc cgcattgcag agataattgt atttaagtgc ctagctcgat     480
acaataaacg ccatt                                                      495

<210> SEQ ID NO 54
<211> LENGTH: 43
<212> TYPE: PRT
<213> ORGANISM: Artificial sequence
<220> FEATURE:
<223> OTHER INFORMATION: Description of Artificial Sequence: Synthetic
      pJV peptide

<400> SEQUENCE: 54

Val Arg Ser Pro Gly Asp Ala Ile His Ala Val Leu Thr Ser Ile Glu
  1               5                  10                  15

Asp Thr Gly Thr Asp Pro Ala Ser Ala Ala Gly Asn Gly Ala Leu Glu
                 20                  25                  30

Arg Gly Phe Pro Val Pro Arg Val Thr His Arg
             35                  40
```

NUCLEIC ACID CONSTRUCTS

FIELD OF THE INVENTION

The invention relates to the fields of molecular biology and immunology and generally to reagents useful in nucleic acid immunisation techniques. More specifically, the invention relates to nucleic acid constructs for the expression of antigenic polypeptides, and to nucleic acid immunisation strategies using such reagents.

BACKGROUND OF THE INVENTION

Gene therapy and nucleic acid immunisation are promising approaches for the treatment and prevention of both acquired and inherited diseases. These techniques provide for the transfer of a desired nucleic acid into a subject with subsequent in vivo expression. Transfer can be accomplished by transfecting the subject's cells or tissues ex vivo and reintroducing the transformed material into the host. Alternatively, the nucleic acid can be administered in vivo directly to the recipient.

Each of these techniques requires efficient expression of the nucleic acid in the transfected cell, to provide a sufficient amount of the therapeutic or antigenic gene product. Several factors are known to affect the levels of expression obtained, including transfection efficiency, and the efficiency with which the gene or sequence of interest is transcribed and the mRNA translated.

A number of expression systems have been described in the art, each of which typically consists of a vector containing a gene or nucleotide sequence of interest operably linked to expression control sequences. These control sequences include transcriptional promoter sequences and transcriptional start and termination sequences. Commonly used promoters for mammalian cell expression systems include the SV40 early promoter, a cytomegalovirus (CMV) promoter such as the CMV immediate early promoter (Chapman et al (1991) *Nucl. Acids Res.* 19:3979-3986), the mouse mammary tumour virus long terminal repeat (LTR) promoter, the adenovirus major late promoter (Ad MLP) and the herpes simplex virus (HSV) promoter, among others. Nonviral promoters, such as a promoter derived from the murine metallothionein gene are also commonly used.

Expression systems often include transcriptional modulator elements, referred to as "enhancers". Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters); and can operate when positioned in either orientation relative to the sequence of interest (Banerji et al. (1981) *Cell* 27:299-308, deVilleirs et al. (1981) *Nucl. Acids Res* 9: 6251-6264). Enhancers have been identified from a number of viral sources, including polyoma virus, BK virus, cytomegalovirus (CMV), adenovirus, simian virus 40 (SV40), Moloney sarcoma virus, bovine papilloma virus and Rous sarcoma virus (deVilleirs et al supra, Rosenthal et al. (1983) *Science* 222: 749-755, Hearing et al (1983) *Cell* 33:695-703, Weeks et al. (1983) *Mol. Cell. Biol.* 3:1222-1234, Levinson et al. (1.982) *Nature* 295:568-572, and Luciw et al. (1983) *Cell* 33: 705-716).

A number of expression systems for nucleic acid immunisation and gene therapy make use of the hCMV immediate early promoter. See eg U.S. Pat. Nos. 5,168,062 and 5,385,839 to Stinski, and EP Patent Specification 0323997 B1. Expression vectors using the hCMV immediate early promoter include for example, pWRG7128 (Roy et al, Vaccine 19, 764-778, 2001), and pBC12/CMV and pJW4303 which are mentioned in WO 95/20660. Chapman et al (1991) report reduced levels of expression from the hCMV immediate early promoter in the absence of hCMV Intron A.

SUMMARY OF THE INVENTION

A nucleic acid construct has been developed using manipulated viral promoter/expression sequences, that provides enhanced expression of heterologous coding sequences in host cells. The construct is suitable for efficient expression of antigen-encoding genes, and can therefore be used in nucleic acid immunisation. In particular, the construct can be provided on carrier particles, for use in particle-mediated nucleic acid immunisation.

Accordingly, the present invention provides a nucleic acid construct comprising a chimeric promoter sequence and a cloning site for insertion of a coding sequence in operable linkage with the chimeric promoter, wherein the chimeric promoter sequence comprises:
  (a) a hCMV immediate early promoter sequence;
  (b) exon 1 and at least a part of exon 2 of the hCMV major immediate early gene; and
  (c) a heterologous intron provided in place of the intron A region of the hCMV major immediate early gene.

The invention also provides:
a nucleic acid construct comprising:
  (i) a chimeric promoter sequence which comprises:
    (a) a hCMV immediate early promoter sequence;
    (b) exon 1 and at least a part of exon 2 of the hCMV major immediate early gene; and
    (c) a heterologous intron provided in place of the intron A region of the hCMV major immediate early gene; and
  (ii) a cloning site for insertion of a coding sequence in operable linkage with the chimeric promoter; and
  (iii) (a) a non-translated leader sequence which is derived from HBV preS2 antigen sequence, HBV e-antigen sequence or HSV type 2gD antigen sequence and which is in operable linkage with the chimeric promoter; and/or
    (b) an enhancer sequence which is derived from a 3' untranslated region (UTR) of a HBsAg sequence, or a 3'UTR of a simian CMV immediate early gene sequence and which is in operable linkage with the chimeric promoter, wherein the enhancer sequence is downstream of the cloning site;

a nucleic acid construct comprising:
  (i) a promoter sequence;
  (ii) a non-translated leader sequence derived from HBV preS2 antigen sequence, HBV e-antigen sequence or HSV type 2 gD antigen sequence; and
  (iii) a coding sequence operably linked to (i) and (ii)
wherein the coding sequence is heterologous to the non-translated leader sequence;

a nucleic acid construct comprising:
  (i) a promoter sequence;
  (ii) a coding sequence operably linked to the promoter sequence (i); and
  (iii) an enhancer sequence 3' of and operably linked to the coding sequence (ii);
wherein the enhancer sequence (iii) is derived from a 3'UTR of an HBsAg sequence or a 3'UTR of a simian CMV immediate early gene sequence, and the coding sequence (ii) is heterologous to the 3' enhancer sequence;
a method of obtaining expression in mammalian cells of a polypeptide of interest, which method comprises transferring into said cells a nucleic acid construct of the invention, the construct including a coding sequence encoding the polypeptide;

coated particles, suitable for delivery from a particle-mediated delivery device, which particles comprise carrier particles coated with a nucleic acid construct of the invention, the construct including a coding sequence encoding the polypeptide;

a dosage receptacle for a particle mediated delivery device comprising the coated particles;

a particle mediated delivery device loaded with the coated particles;

a method of nucleic acid immunisation comprising administering to a subject an effective amount of the coated particles in which particles the coding sequence encodes an antigen;

a purified isolated chimeric promoter sequence which comprises:

(a) a hCMV immediate early promoter sequence;
(b) exon 1 and at least a part of exon 2 of the hCMV major immediate early gene; and
(c) a heterologous intron provided in place of the intron A region of the hCMV major immediate early gene.

These and other objects, aspects, embodiments and advantages of the present invention will readily occur to those of ordinary skill in the art in view of the disclosure herein.

BRIEF DESCRIPTION OF THE DRAWINGS

FIG. 13 sets out the base composition of pJV7563 (DNA disclosed as SEQ ID NO:14; peptide sequence as SEQ ID NO:54).

BRIEF DESCRIPTION OF THE SEQUENCES

Figure 1:
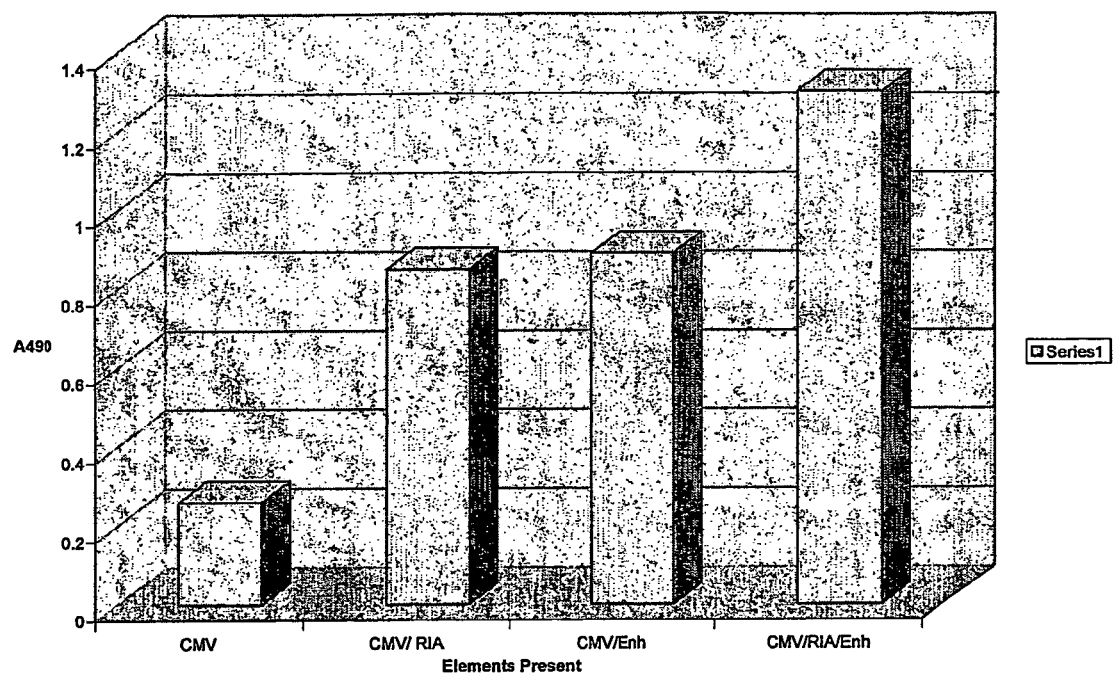
FIG. 1 illustrates the levels of expression of hepatitis B virus surface antigen (HBsAg) obtained using various plasmid expression vectors.

SEQ ID NO:1 is hCMV immediate early promoter sequence (GenBank #M60321, X17403)

SEQ ID NO:2 is sequence from exons 1 and 2 of the hCMV major immediate early gene (GenBank. #M60321, X17403)

SEQ ID NO:3 is rat insulin intron A sequence (GenBank #J00748)

SEQ ID NO:4 is the sequence of a chimeric promoter according to the present invention SEQ ID NO:5 is a leader sequence from HBV preS2 antigen 5' UTR sequence (GenBank #M54923)

SEQ ID NO:6 is a leader sequence from HSV type 2 gD 5'UTR sequence (GenBank #Z86099)

SEQ ID NO:7 is a leader sequence from HBV e antigen 5'UTR sequence (GenBank #M54923)

SEQ ID NO:8 is HBVenh 3'UTR sequence (GenBank #AF143308)

SEQ ID NO:9 is simian immediate early gene 3'UTR sequence (GenBank #M16019)

SEQ ID NO:10 is rabbit β globin poly A sequence (GenBank #K03256)

SEQ ID NO:11 is simian sCMV immediate early gene poly A sequence (GenBank #M16019)

SEQ ID NO:12 is HSV2 gB gene poly A sequence (GenBank #Z86099):

SEQ ID NO:13 is HPV16 early gene poly A sequence (GenBank #K02718)

SEQ ID NO:14 is the sequence of the pJV expression vector

SEQ ID NO:15 is PCR primer JF93
SEQ ID NO:16 is PCR primer F110
SEQ ID NO:17 is PCR primer GW1
SEQ ID NO:18 is PCR primer JF254
SEQ ID NO:19 is PCR primer GW150
SEQ ID NO:20 is PCR primer JF255
SEQ ID NO:21 is PCR primer DS1
SEQ ID NO:22 is PCR primer DA1
SEQ ID NO:23 is PCR primer JF301
SEQ ID NO:24 is PCR primer JF302
SEQ ID NO:25 is PCR primer JF84
SEQ ID NO:26 is PCR primer JF225
SEQ ID NO:27 is PCR primer JF335
SEQ ID NO:28 is PCR primer JF336
SEQ ID NO:29 is PCR primer JF357
SEQ ID NO:30 is PCR primer JF365
SEQ ID NO:31 is PCR primer JF393
SEQ ID NO:32 is PCR primer JF406
SEQ ID NO:33 is PCR primer JF256
SEQ ID NO:34 is PCR primer JF257
SEQ ID NO:35 is PCR primer JF320
SEQ ID NO:36 is PCR primer JF321
SEQ ID NO:37 is PCR primer JF386
SEQ ID NO:38 is PCR primer FcAS
SEQ ID NO:39 is oligonucleotide JF354
SEQ ID NO:40 is PCR primer JF355
SEQ ID NO:41 is PCR primer JF356
SEQ ID NO:42 is oligonucleotide JF348
SEQ ID NO:43 is PCR primer JF349
SEQ ID NO:44 is PCR primer JF350
SEQ ID NO:45 is oligonucleotide JF351
SEQ ID NO:46 is PCR primer JF352
SEQ ID NO:47 is PCR primer JF353
SEQ ID NO:48 is PCR primer JF430
SEQ ID NO:49 is PCR primer JF442
SEQ ID NO:50 is PCR primer JF421
SEQ ID NO:51 is PCR primer JF444
SEQ ID NO:52 is Pseudorabies virus (PRV) promoter sequence.
SEQ ID NO:53 is Rous sarcoma virus (RSV) promoter sequence.

DETAILED DESCRIPTION

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology*, 2nd Edition, vol. I & II (B. N. Fields and D. M. Knipe, eds.).

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise.

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

The term "nucleic acid immunization" is used herein to refer to the introduction of a nucleic acid molecule encoding one or more selected antigens into a host cell for the in vivo expression of the antigen or antigens. The nucleic acid molecule can be introduced directly into the recipient subject, such as by standard intramuscular or intradermal injection; transdermal particle delivery; inhalation; topically, or by oral; intranasal or mucosal modes of administration. The molecule alternatively can be introduced ex vivo into cells which have been removed from a subject. In this latter case, cells containing the nucleic acid molecule of interest are re-introduced into the subject such that an immune response can be mounted against the antigen encoded by the nucleic acid molecule. The nucleic acid molecules used in such immunization are generally referred to herein as "nucleic acid vaccines."

The term "adjuvant intends an material or composition capable of specifically or non-specifically altering, enhancing, directing, redirecting, potentiating or initiating an antigen specific immune response. Thus, coadministration of an adjuvant with an antigen may result in a lower dose or fewer dose of antigen being necessary to achieve a desired immune response in the subject to which the antigen is administered, or coadministration may result in a qualitatively and/or quantitatively different immune response in the subject. In particular, the administration of the adjuvant may result in an enhanced immune response such as one of greater magnitude and/or duration. The effectiveness of an adjuvant can be determined by administering the adjuvant with a vaccine composition in parallel with a vaccine composition alone to animals and comparing antibody and/or cellular mediated immunity in the two groups using standard assays such as radioimmunoassay, ELISAs, and CTL assays.

By "core carrier" is meant a carrier on which a guest nucleic acid (e.g., DNA, RNA) is coated in order to impart a defined particle size as well as a sufficiently high density to achieve the momentum required for cell membrane penetration, such that the guest molecule can be delivered using particle-mediated techniques (see, e.g., U.S. Pat. No. 5,100,792). Core carriers typically include materials such as tungsten, gold, platinum, ferrite, polystyrene and latex. See e.g., *Particle Bombardment Technology for Gene Transfer*, (1994) Yang, N. ed., Oxford University Press, New York, N.Y. pages 10-11.

By "needleless syringe" is meant an instrument which delivers a particulate composition transdermally without the aid of a conventional needle to pierce the skin. Needleless syringes for use with the present invention are discussed herein.

The term "transdermal" delivery intends intradermal (e.g., into the dermis or epidermis), transdermal (e.g., "percutaneous") and transmucosal administration, i.e., delivery by passage of an agent into or through skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdermal Delivery of Drugs*, Vols. 1-3, Kydonieus and Berner (eds.), CRC Press, (1987). Thus, the term encompasses delivery from a needleless syringe as described in U.S. Pat. No. 5,630,796, as well as particle-mediated delivery as described in U.S. Pat. No. 5,865,796.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

An "antigen" refers to any agent, generally a macromolecule, which can elicit an immunological response in an individual. The term may be used to refer to an individual macromolecule or to a homogeneous or heterogeneous population of antigenic macromolecules. As used herein, "antigen" is generally used to refer to a protein molecule or portion thereof which contains one or more epitopes. For the purposes of the present invention, antigens can be obtained or derived from any appropriate source. Furthermore, for the purposes of the present invention, an "antigen" includes a protein having modifications, such as deletions, additions and substitutions (generally conservative in nature) to the native sequence, so long as the protein maintains sufficient immunogenicity. These modifications may be deliberate, for example through site-directed mutagenesis, or may be accidental, such as through mutations of hosts which produce the antigens.

An "immune response" against an antigen of interest is the development in an individual of a humoral and/or a cellular immune response to that antigen. For purposes of the present invention, a "humoral immune response" refers to an immune response mediated by antibody molecules, while a "cellular immune response" is one mediated by T-lymphocytes and/or other white blood cells.

The terms "nucleic acid molecule" and "polynucleotide" are used interchangeably herein and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term nucleic acid sequence is the alphabetical representation of a polynucleotide molecule. This alphabetical representation can be input into databases in a computer having a central processing unit and used for bioinformatics applications such as functional genomics and homology searching.

A "vector" is capable of transferring nucleic acid sequences to target dells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors. A "plasmid" is a vector in the form of an extrachromosomal genetic element.

A nucleic acid sequence which "encodes" a selected antigen is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, procaryotic or eucaryotic mRNA, genomic sequences from viral or procaryotic DNA or RNA, and even synthetic DNA sequences. A transcription termination sequence may be located 3' to the coding sequence.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

"Operably linked" refers to an arrangement of elements wherein the components so described are configured so as to perform their usual function. Thus, a given promoter operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

"Recombinant" is used herein to describe a nucleic acid molecule (polynucleotide) of genomic, cDNA, semisynthetic, or synthetic origin which, by virtue of its origin or manipulation is not associated with all or a portion of the polynucleotide with which it is associated in nature and/or is linked to a polynucleotide other than that to which it is linked in nature. Two nucleic acid sequences which are contained within a single recombinant nucleic acid molecule are "heterologous" relative to each other when they are not normally associated with each other in nature.

Homologues of polynucleotides are referred to herein. Typically a polynucleotide which is homologous to another polynucleotide is at least 70% homologous to the polynucleotide, preferably at least 80 or 90% and more preferably at least 95%, 97% or 99% homologous thereto. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60 or 100 or more contiguous nucleotides.

Methods of measuring polynucleotide homology or identity are known in the art. For example the UWGCG Package provides the BESTFIT program which can be used to calculate homology (e.g. used on its default settings) (Devereux et al (1984) *Nucleic Acids Research* 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National-Centre for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl, Acad. Sci.* USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologues typically hybridize with the relevant polynucleotide at a level significantly above background. The signal level generated by the interaction between the homologue and the polynucleotide is typically at least 10 fold, preferably at least 100 fold, as intense as "background hybridisation". The intensity of interaction may be measured, for example, by radiolabelling the probe, e.g. with $^{32}$P. Selective hybridisation is typically achieved using conditions of medium to high stringency, (for example, 0.03M sodium chloride and 0.003M sodium citrate at from about 50° C. to about 60° C.

Stringent hybridization conditions can include 50% formamide, 5×Denhardt's Solution, 5×SSC, 0.1% SDS and 100 μg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art. See, e.g., Sambrook et al., supra.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue. Where a polynucleotide encodes a polypeptide, substitutions preferably create "conservative" changes in the amino acid encoded. These are defined according to the following table. Amino acids in the same block in the second column and preferably in the same line in the third column may be substituted for each other in conservative changes.

| ALIPHATIC | Non-Polar | G A P |
| | | I L V |
| | Polar-uncharged | C S T M |
| | | N Q |
| | Polar-charged | D E |
| | | K R |
| AROMATIC | | H F W Y |

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly.

B. General Overview

The invention is concerned with nucleic acid constructs which allow efficient expression of heterologous coding sequences, and in particular antigen-encoding genes, in host cells. More specifically, the invention provides nucleic acid constructs comprising, or in some embodiments, consisting essentially of a chimeric promoter sequence and a cloning site, such that when a coding sequence is inserted in the cloning site, the coding sequence is in operable linkage with the chimeric promoter.

The chimeric promoter comprises, or in some embodiments consists essentially of:
 (a) a hCMV immediate early promoter sequence;
 (b) exon 1 and at least a part of exon 2 of the hCMV major immediate early gene; and
 (c) a heterologous intron provided in place of the intron A region of the hCMV major immediate early gene.

The hCMV immediate early promoter sequence (a) may comprise:
 (i) a native hCMV immediate early promoter sequence;
 (ii) a functional homologous variant thereof; or
 (iii) a functional fragment of (i) or (ii).

In general sequence (a) comprises about 100 to 600, preferably 200 to 600, for instance 400 to 600 nucleotides. Typically sequence (a) comprises the sequences present in (i) which bind transcription factors or the RNA polymerase, or instead of any of these sequences, homologues of these sequences able to bind the same transcription factors and RNA polymerase. Typically such sequences or their homologues are present in promoter sequence (a) in the same order and/or substantially the same relative spacing as in (i).

Generally, (i) comprises at least from nucleotides −100 to −1, typically −150 to −1, for example −500 to −1 or −600 to −1 of the hCMV major immediate early gene. Sequence (i) typically comprises the hCMV core promoter sequence and may also include one or more enhancer elements present in hCMV immediate early promoter. For example, (i) may comprise from nucleotides −118 to −1, or −524 to −1 as in U.S. Pat. No. 6,218,140, or from nucleotides −62 to 1 or −465 to −1 as in U.S. Pat. No. 5,385,839.

Generally (i) includes a TATA box or CAAT box commonly found in promoter sequences. Preferably the sequence includes one or more of the repeat sequences in the hCMV immediate early promoter.

In a preferred embodiment, (i) comprises SEQ ID NO: 1.

A hCMV immediate early promoter sequence can be obtained using known methods. A native hCMV immediate early promoter can be isolated directly from a sample of the virus, using standard techniques. U.S. Pat. No. 5,385,839, for example, describes the cloning of a hCMV promoter region. The sequence of a hCMV immediate early promoter is available at Genbank #M60321 (hCMV Towne strain) and X17403 (hCMV Ad169 strain). A native sequence could therefore be isolated by PCR using PCR primers based on the known sequence. See e.g Sambrook et al, supra, for a description of techniques used to obtain and isolate DNA. A suitable hCMV promoter sequence could also be isolated from an existing plasmid vector. Promoter sequences can also be produced synthetically.

A functional variant (ii) or fragment (iii) is generally one which retains and/or complements the activity of the native promoter (i). Typically this activity is the ability to cause (including initiating and regulating) transcription of an operably linked polynucleotide, in particular the hCMV major immediate early gene. In one embodiment, the variant or fragment would be able to complement the activity of the native promoter in a hCMV virus, for example allowing the virus to retain the ability to infect and/or replicate in cells.

A homologous variant (ii) or fragment (iii) can be assayed for the ability to retain and/or complement the activity of (i). For example, a variant or fragment may be assayed for ability to restore functionality (such as infection and/or replication ability) to mutant hCMV in which the native hCMV immediate early promoter is defective.

A homologous variant (ii) or fragment (iii) may be tested for utility using the Comparative Expression Assay below. The test promoter sequence is swapped into the base vector in place of the native hCMV immediate early promoter. Typically, a functional variant or fragment allows at least 50%, for instance, 60, 70, 80, 90% or more of the expression provided using the base vector. Generally expression is provided in at least one but preferably two reference cell types. Typically, the reference cells are mammalian HEK 293T, CHO, HeLa, BHK, 3T3 or COS cells.

Additionally or alternatively, promoter sequence may be tested in the Comparative Immunogenicity Assay below. Test promoter sequence is swapped into the base vector in place of the native hCMV immediate early promoter. A functional promoter sequence provides antibody titres that are at least as high as or higher than those achieved by the base vector with at least one, preferably two antigens. Preferably antibody titres are at least 5%, 10%, 20%, 30% or 40% higher than with the base vector. Preferred antigens are HBsAg, HSV 2gD and flu-M2 antigens. According to this assay, a functional homologous variant (ii) or functional fragment (iii) of native promoter sequence (i) is one which allows the highest antibody titres achieved by the native sequence.

As mentioned above, the construct may comprise exon sequence (b) which comprises sequence derived from exon 1 and exon 2 of the hCMV major immediate early gene. Exons are coding sequences, which in nature are generally separated by introns. In the native hCMV major immediate early gene, exons 1 and 2 are usually separated by the native intron A. In the present chimeric construct exon 2 sequence is generally positioned 3' of exon 1 sequence, without intervening intron sequence, so that the exon 1 and exon 2 sequences are contiguous.

Exon sequence (b) may comprise:
  (i) native exon sequence, typically exon 1 and (whole or partial) exon 2;
  (ii) a homologous variant of (i) which is functional; or
  (iii) a functional fragment of (i) or (ii).

Sequence (i) may comprise from about 50 to 100% of the native hCMV major immediate early gene exon 1 sequence, for example, 60 to 90% or 70 to 80%. Typically at least 50% of the natural exon 1 sequence is present, such as 60%, 70%, 80%, 90% or more. Exon sequence (b) also comprises at least a part of exon 2 sequence. In sequence (i), typically 2 or more bases of native exon 2, for example 2 to 9, 2 to 7 or 3 to 5 bases are present. Up to and including 100% of natural exon 2 sequence, for example 5 to 95%, 20 to 80% or 40 to 60% of natural exon 2 sequence may be present. Typically the homologous variant has any of the above lengths mentioned for the native sequence.

Preferably (i) comprises SEQ ID No. 2.

Suitable exon sequence (b) can be obtained using known methods. See e.g Sambrook et al., supra, for a description of techniques used to obtain and isolate DNA. Native hCMV major immediate early gene sequence can be isolated directly from a sample of the virus, using standard techniques (see for example, MacLean, A (1998) "Preparation of HSV-DNA and Production of Infectious Virus" in Herpes Simplex Virus Protocols S. Brown, A Maclean, editors, Humana Press, Totowa, N.J., pp. 19-26). The sequence of a hCMV major immediate early gene, including the location of exon 1 and exon 2, is available at Genbank #M60321, X17403. Native exon 1 and 2 sequences could therefore be isolated by cutting the native major gene sequence at appropriate restriction sites or by PCR using PCR primers based on the known sequence. Suitable exon sequences could alternatively be isolated from an existing plasmid vector, such as pWRG7128. Exon sequences can also be produced synthetically, rather than cloned. Variant sequences can readily be constructed by routine methodologies such as site-directed mutagenesis.

Generally the exon sequence will, when present in the construct of the invention, enhance expression, typically causing comparable enhancement to the native exon 1 and exon 2 sequence (i) mentioned above.

Exon sequence may be assayed for functionality using the Comparative Expression Assay below. Test exon sequence is swapped into the base vector in place of the exon sequence already present. Generally exon sequence is functional if the sequence does not abrogate expression but preferably increases expression in at least one but preferably two reference cell types when compared to the base vector. Typically the reference cells are mammalian HEK293T, CHO, HeLa, BHK, 3T3 or COS cells. Preferably expression increases by at least 5%, 10%, 20%, 30% or 40%. According to this assay, a functional homologous variant (ii) or functional fragment (iii) of natural exon sequence (i) is one which allows at least 50% of the expression improvement provided by, the natural sequence.

Additionally or alternatively, exon sequence may be tested in the Comparative Immunogenicity Assay below. Test exon sequence is swapped into the base vector in place of the exon sequence already present. Functional exon sequence provides antibody titres that are at least as high as or higher than those achieved by the base vector with at least one, preferably two antigens. Preferably antibody titres are at least 5%, 10%, 20%, 30% or 40% higher than with the base vector. Preferred antigens are HBsAg, HSV 2gD and flu-M2 antigens. According to this assay, a functional homologous variant (ii) or functional fragment (iii) of natural exon sequence (i) is one which allows the highest antibody titres achieved by the natural sequence.

The chimeric promoter construct comprises heterologous intron (c) in place of the native intron A region of the hCMV major immediate early gene. An intron is a non-coding sequence which is spliced from the hnRNA transcribed from a gene. A heterologous intron is one which is not present in the coding sequence in nature.

The heterologous intron (c) replaces wholly or partially, native intron A of the hCMV major immediate early gene. Typically the native intron A is absent.

In general the heterologous intron (c) is 3' of exon sequence (b).

Typically the heterologous intron (c) comprises:
  (i) a natural intron;
  (ii) a functional homologous variant of (i); or
  (iii) a functional fragment of (i) or (ii).

Heterologous intron (c) is in general a viral or eukaryotic intron. Preferably the intron is a mammalian intron, in particular a non-human intron, for example a rat or chicken intron. Preferably the intron is an intron A, for example, rat insulin intron A, chicken keratin intron A or chicken cardiac action intron A.

Typically intron (c) has a length of from about 50 nucleotides to about 1000 nucleotides, for instance from about 100 to about 500 nucleotides. The intron (c) may for example, comprise 50 to 500 nucleotides, such as up to 100, 200, 300 or 400 nucleotides. Preferably the intron comprises sequence found at about nucleotides 50 to 133 of native rat insulin intron A, or a homologue of this sequence.

Preferably heterologous intron (c) is capable of being spliced from an RNA transcript in a eukaryotic host cell. In general the intron comprises one or more of a donor sequence (such as GT), an acceptor sequence (such as AG), a 3' pyrimidine rich region and a branch point sequence. The pyrimidine rich region, if present, may include, for example at least 5, 8, 10 or more pyrimidines. Preferably the intron comprises at least a donor sequence, acceptor sequence and a branch point sequence. Typically in the chimeric construct, intron (c) comprises non-intron flanking sequences which are derived from exon sequences found on the intron/exon boundaries of the natural intron (i). The flanking exon sequence may be native exon sequence or a homologue of this sequences which retains substantially the same activity as the native sequence, for example retains splicing function. Typically from 5 to 10, preferably from 7 to 10 bases of exon sequence are included at each end of the intron.

Intron (c) may be an artificial intron, provided that the intron is functional. For example, a recombinant or chimeric intron may be used. Such an intron may comprise sequence from more than one natural intron.

Typically intron (c) comprises sequences present in hCMV intron A which bind transcription factors or regulatory proteins or instead of any of these sequences, homologues of these sequences able to bind the same factors or proteins. Typically such sequences or their homologues are present in the intron (c) in the same order and/or substantially the same relative spacing as in hCMV intron A.

Intron (c) may comprise an homologous variant (ii) in which the sequence of the natural intron (i) has been modified to remove an internal restriction site. For example, an homologous variant of rat insulin intron A may be used in which an internal NheI site has been destroyed.

Preferably, intron (c) comprises:
(i) SEQ ID No. 3;
(ii) a functional homologous variant of (i); or
(iii) a functional fragment of (i) or (ii).

Intron sequence (c) may be obtained using standard cloning techniques. For example, rat insulin intron A sequence is available at GenBank J00748, chicken keratin intron A sequence at GenBank J00847 and chicken cardiac intron A sequence at GenBank X02212. Intron sequence can be isolated from natural sources using primers based on known sequence. Sequence may be prepared synthetically. Variant sequencer may be obtained by mutagenesis.

Typically a functional intron sequence, for example a functional variant (ii) or a functional fragment (iii) is one which has substantially the same activity as, and/or complements the activity of a natural intron (i). In one embodiment the activity is splicing activity.

Intron (c) sequences may be tested for splicing activity using a routine splicing assay. In general a functional homologue (ii) or functional fragment (iii) will show at least 50%, for example 60%, 70%, 80%, 90% and up to 100% or more of the splicing efficiency of the natural intron (i) in the assay.

In general the heterologous intron sequence will, when present in the construct of the invention, enhance expression. Typically, a variant (ii) or fragment (iii) intron will cause comparable enhancement to a natural intron (i).

Functionality of potential intron sequence (c) can be tested using the Comparative Expression Assay below. The heterologous intron is swapped into the base vector. Generally heterologous intron sequence is functional if the addition of the sequence increases expression in at least one, but preferably two reference cell types by 25% or more, compared to the base vector. Typically the reference cells are mammalian HEK293T, CHO, HeLa, BHK, 3T3 or COS cells. The increase in expression may be at least 35%, 45%, 55% or more. According to this assay, a functional variant (i) or functional fragment (ii) of a natural intron sequence (i) is one which allows greater than 50% of the expression improvement achieved by the natural sequence.

A heterologous intron (c) sequence may, additionally or alternatively be tested for functionality using the Comparative Immunogenicity Assay below. Intron (c) sequence is added to the base vector. A functional intron (c) sequence provides antibody titres that are higher than those achieved by the base vector with at least one, preferably two antigens. Preferably, the antibody titres are at least 5 or 10%, for instance 20%, 30% or 40% higher than with the base vector.

Preferred antigens are HBsAg, HSV2gD and Flu-M2 antigens. According to this assay, a functional variant (ii) or functional fragment (iii) of a natural intron sequence (i) is one which allows the highest antibody titres achieved by the natural sequence.

Suitable heterologous intron sequence can be obtained using standard cloning techniques. For example, rat insulin intron A sequence is available at GenBank J00748, chicken keratin intron A at GenBank J00847, and chicken cardiac actin intron A at X02212. Intron sequence can be isolated from native sources using primers based on the known sequence data. Suitable sequence may also be prepared synthetically.

The component sequences (a), (b) and (c) may be provided suitably linked together to form a chimeric promoter using standard cloning or molecular biology techniques. Preferably intron sequence (c) is provided 3' of exon sequence (b). The chimeric promoter construct is linked to a cloning site, in such a way that the promoter will effect the expression of a coding sequence inserted in the site, when the proper enzymes are present. Suitable cloning sites, including multi-cloning sites are known in the art, e.g the pUC19, pBC SK, pBluescript II KS, cDNA3.1, pSP72, pGEM 7Z multicloning site.

Typically, a nucleic acid for insertion (or inserted) in the cloning site encodes a therapeutically relevant polypeptide. It is preferred that the coding sequence is suitable for use in nucleic acid immunisation or gene therapy. The nucleic acid insert may thus comprise a sequence capable of providing immunity, for example an immunogenic sequence that elicits a humoral and/or cellular immune response when delivered to a subject. Alternatively, the nucleic acid may comprise one or more genes encoding a therapeutic polypeptide e.g a protein defective or missing from a target cell genome or a non-native protein having a desired biological or therapeutic effect (e.g., an antiviral function). For the treatment of genetic disorders, functional genes corresponding to genes known to be deficient in the particular disorder can be administered to a subject. Preferably the nucleic acid is DNA.

Suitable nucleic acids for insertion include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemia and hemophilia; genetic defects such as cystic fibrosis, Gaucher's Disease, adenosine deaminase (ADA) deficiency, emphysema, etc.

For example, in methods for the treatment of solid tumors, genes encoding toxic peptides (i.e., chemotherapeutic agents such as ricin, diptheria toxin and cobra venom factor), tumor suppressor genes such as p53, genes coding for mRNA sequences which are antisense to transforming oncogenes, antineoplastic peptides such as tumor necrosis factor (TNF) and other cytokines, or transdominant negative mutants of transforming oncogenes, can be inserted for expression at or near the tumor site.

Similarly, nucleic acids coding for polypeptides known to display antiviral and/or antibacterial activity, or stimulate the host's immune system, can also be included. The nucleic acid may encode one of the various cytokines (or functional fragments thereof), such as the interleukins, interferons and colony stimulating factors. The nucleic acid may encode an antigen for the treatment or prevention of a number of conditions including but not limited to cancer, allergies, toxicity and infection by a pathogen such as, but not limited to, fungus, viruses including Human Papilloma Viruses (HPV), HIV, HSV2/HSV1, influenza virus (types A, B and C), Polio virus, RSV virus, Rhinoviruses, Rotaviruses, Hepatitis A virus, Norwalk Virus Group, Enteroviruses, Astroviruses, Measles virus, Par Influenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; bacteria including *M. tuberculosis, Chlamydia, N. gonorrhoea, Shigella, Salmonella, Vibrio Cholera, Treponema pallidua, Pseudomonas, Bordetella pertussis, Brucella, Franciscella tulorensis, Helicobacter pylori, Leptospria interrogaus, Legionella pnumophila, Yersinia pestis, Streptococcus* (types A and B), *Pneumococcus, Meningococcus, Hemophilus influenza* (type b), *Toxoplama gondic, Complybacteriosis, Moraxella catarrhalis, Donovanosis, and Actinomycosis*; fungal pathogens including *Candidiasis* and *Aspergillosis*; parasitic pathogens including *Taenia, Flukes, Roundworms, Amebiasis, Giardiasis, Cryptosporidium, Schitosoma, Pneumocystis carinii, Trichomoniasis* and *Trichinosis*. The nucleic acid my also be used to provide a suitable immune response against numerous veterinary diseases, such as Foot and Mouth diseases, Coronavirus, *Pasteurella multocida, Helicobacter, Strongylus vulgaris, Actinobacillus pleuropneumonia*, Bovine viral diarrhea virus (BVDV), *Klebsiella pneumoniae, E. Coli, Bordetella pertussis, Bordetella parapertussis* and *Bordetella brochiseptica*. Thus in one-aspect, the nucleic acid constructs of the present invention may find use in a vaccine.

In some embodiments, the nucleic acid construct will encode an adjuvant. Thus, the sequences inserted into the cloning site for insertion of a coding sequence may encode a polypeptide that can act as an adjuvant. In a preferred instance, the encoded adjuvant may be an ADP-ribosylating bacterial toxin. These include diphtheria toxin (DT), pertussis toxin (PT), cholera toxin (CT), the *E. coli* heat labile toxins (LT1 and LT2), *Pseudomonas* endotoxin A, *Pseudomonas* exotoxin S, *B. cereus exoenzyme, B. sphaericus toxin, C botulinum* C2 and C3 toxins, *C. limosum* exoenzyme, as well as toxins from *C. perfringens, C spiriforma* and *C. difficile* and *Staphylococcus aureus* EDIN. Most ADP-ribosylating bacterial toxins contain A and B subunits. The construct may express the A subunit, the B subunit and/or both subunits.

In a preferred instance, the nucleic acid construct may encode the *E. coli* heat labile toxin and/or cholera toxin and in particular may express *E. coli* heat labile toxin. A GenBank entry for the complete sequences of the CT subunit A and B genes can be found at Locus VIBCTXABB (Accession No. D30053), while a GenBank entry for the complete sequences of the LT subunit A and B genes can be found at locus AB0116677 (Accession No. AB011677).

The construct may express an active variants or fragment of a particular adjuvant. The variant or fragment will be said to be active if it retains at least some of the adjuvant activity of the polypeptide it is derived from. Thus, the variant and/or fragment will still be able to enhance an immune response against a particular antigen in comparison to the immune response seen when no adjuvant is administered with the antigen. The encoded sequence may be active fragments or variants of CT A and/or B subunits and in particular may be active fragments of LT A and/or B subunits.

The toxin subunit may have had its naturally occurring signal sequence deleted. A naturally occurring exotoxin subunit may have been modified to detoxify the toxin. The A subunit may have been modified to disrupt or inactivate ADP-ribosyl transferase activity.

Thus, the adjuvant constructs of the invention may be used to enhance an immune response against a particular antigen. The enhanced immune response may involve an immune response of greater magnitude or duration. In may mean that when the antigen is re-encountered the immune response then is greater than if no adjuvant was administered. The enhance immune response may result in higher antibody titres. In the case of some constructs, and in particular those expressing exotoxin subunits the adjuvant may result in an augmented cellular response and a T helper 1-like immune response against the antigen in question.

The nucleic acid for insertion into the cloning site may comprise a polyadenylation (polyA) sequence. Such a polyA sequence is generally native to the coding sequence. Alternatively, a heterologous polyA sequence may be provided in the nucleic acid construct of the invention. Typically the polyA sequence will be provided downstream of the cloning site, such that it is operatively linked to a coding sequence inserted in the cloning site. Any suitable polyA sequence may be included in the construct using standard cloning techniques. Such polyA sequences are known in the art.

The poly A sequence may be:

(i) a natural poly A sequence;

(ii) a functional homologous variant of (i); or (iii) a functional fragment of (i) or (ii).

The natural poly A sequence (i) may be, for example a rabbit β globin gene poly A, Human Papilloma Virus (HPV) early or late gene poly A, HSV-2gB gene poly A, a simian CMV immediate early gene poly A or HSV gD late gene poly A.

Preferably the natural poly A sequence (i) is selected from the group consisting of SEQ ID No. 10 (GenBank K03256), SEQ ID No. 11 (GenBank M16019), SEQ ID No. 12 (GenBank Z80699) and SEQ ID No. 13 (GenBank K02718).

In general, a functional polyA sequence is one which retains polyadenylation activity.

A poly A sequence may be tested for the ability to bring about polyadenylation of an RNA transcript using a routine expression assay. A functional homologous variant (ii) or functional fragment (iii) typically shows at least 50%, for example 60%, 70% 80% or more of the poly A activity of the natural poly A sequence in the assay.

Generally the poly A sequence will, when present in the construct of the invention, enhance expression, typically causing comparable enhancement to the natural poly A sequence (i) mentioned above.

A poly A sequence may also be assayed for functionality using the Comparative Expression Assay below. A test poly A region is swapped into the base vector in place of the RBGpA. A test poly A is considered functional if the poly A does not abrogate expression but preferably increases expression in at least one but preferably two reference cell types, compared to the base vector. Preferably there is an increase in expression of at least 5%, 10%, 20%, 30%, 40% or 50% or more. Preferred cell types are mammalian HEK293T, CHO, HeLa, BHK, 3T3 or COS cells. According to the assay, an homologous variant (ii) or fragment (iii) is functional if it allows greater than 50% of the expression improvement achieved by the natural poly A sequence (i).

Alternatively, or additionally, poly A sequences may be tested for activity in the Comparative Immunogenicity Assay below. Poly A sequence is swapped into the base vector in place of RBGpA. A functional poly A sequence provides antibody titres that are at least as high as or higher than those achieved by the base vector with at least one, preferably two antigens. Preferably the antibody titres are at least 5%, 10%, for instance 20%, 30% or 40% higher than those achieved with the base vector. Preferred antigens are HBsAg, HSV2gD and Flu-M2 antigens. An homologous variant (ii) or fragment (iii) is functional if it allows the highest antibody titres achieved by the natural poly A sequence (i).

The nucleic acid construct may comprise additional control sequences which influence expression of a coding sequence inserted in the cloning site. The construct may include a non-translated leader sequence. The sequence is provided in the construct in operable linkage with the chimeric promoter, and therefore also with a coding sequence inserted at the cloning site. The leader provides a translational start site for expression of an inserted coding sequence and typically includes a Kozak sequence.

Typically the untranslated leader sequence comprises:
(i) a natural untranslated leader sequence;
(ii) a functional homologous variant of (i); or
(iii) a functional fragment of (i) or (ii).

In general the natural sequence (i) is a eukaryotic sequence or a viral sequence, in particular, of a virus which infects a eukaryote. Preferably the natural sequence (i) is, HBV or HSV sequence, for example HBV preS2 antigen sequence, HBV e-antigen sequence, or HSV type 2gD antigen sequence. Particularly preferably, (i) is selected from the group consisting of SEQ ID No. 5, SEQ ID No. 6 and SEQ ID No. 7.

Typically the leader sequence comprises sequences present in (i) which bind transcription components or regulatory proteins, or homologues of these sequences which are able to bind the same components or proteins. Typically such sequences or their homologues are present in the leader sequence in the same order and/or substantially the same relative spacing, as in (i). In general the leader sequence comprises a translational start site for expression of an inserted coding sequence. Typically the leader sequence includes a Kozak sequence.

In general the untranslated leader sequence has a length of from about 10 to about 200 nucleotides, for example from about 15 to 150 nucleotides, preferably 15 to about 130 nucleotides. Leader sequences comprising, for example, 15, 50, 75 or 100 nucleotides may be used.

Generally a functional untranslated leader sequence is one which is able to provide a translational start site for expression of a coding sequence in operable linkage with the leader sequence. Typically a functional variant (ii) or fragment (iii) has substantially the same activity as and/or complements the activity of the natural sequence (i), usually in facilitating or enhancing expression of a coding sequence in operable linkage with the sequence.

A variant (ii) or fragment (iii) may be tested for activity as an untranslated leader sequence relative to natural leader sequence using standard protocols. For example, expression vectors may be prepared comprising a natural leader sequence (i) operably linked to its native coding sequence, and expression monitored in suitable host cells e.g. mammalian HEK 293T, CHO, HeLa, BHK, 3T3 or COS cells. Test constructs may be prepared in which the natural leader sequence is replaced by an homologous variant or fragment and expression is monitored again in the same host cells. In general, a variant (ii) or fragment (iii) provides at least 50%, such as 60%, 70%, 80%, 90% or 100% or more of the expression provided by the natural sequence.

A potential leader sequence can also be tested for utility in the Comparative Expression Assay below. A test leader sequence is swapped into the base vector in place of the HBV preS2 5'UTR. A functional leader sequence does not abrogate expression but preferably increases expression in at least one but preferably two reference cell types, compared to the base vector. In general expression is increased by at least 5%, 10%, 20%, 30%, 40% or 50%. Preferred cell types are mammalian HEK293T, CHO, HeLa, BHK, 3T3 or COS cells. According to the assay, an homologous variant (ii) or fragment (iii) is functional if it allows greater than 50% of the expression improvement achieved by the natural leader sequence.

Alternatively, or additionally, a leader sequence may be tested for activity in the Comparative Immunogenicity Assay below. A leader sequence is swapped into the base vector in place of HBV preS2 5'UTR. A functional leader sequence provides antibody titres that are at least as high as or higher than those achieved by the base vector, with at least one preferably two antigens. Preferably the antibody titres are at least 5%, 10%, 20%, 30% or 40% higher than with the base vector. Preferred antigens are HBsAg, HSV 2gD and Flu-M2 antigens. An homologous variant (ii) or fragment (iii) is functional if it allows the highest antibody titres allowed by the natural leader sequence (i).

Suitable leader sequence can be obtained using standard protocols. For example, HBV preS2 antigen sequence, HBV e-antigen sequence and HSV type 2gD antigen sequence is available at GenBank M54923, M54923 and Z86099 respectively. Primers can be designed based on this known sequence and used to isolate homologous sequences. Leader sequences may be synthesised based on known sequences.

The nucleic acid construct may comprise an enhancer sequence. An enhancer sequence is typically provided 3' of the cloning site, in operable linkage with both the chimeric promoter and an inserted coding sequence, and acts to increase transcription of the inserted sequence.

In general the enhancer comprises:
(i) a natural enhancer;
(ii) a functional homologous variant of (i); or
(iii) a functional fragment of (i) or (ii).

The enhancer sequence generally comprises from about 50 to about 850 nucleotides, for example from about 75 to about 500 nucleotides. Enhancers of about 100, 200, 300 or 400 nucleotides may be used.

Typically (i) is a eukaryotic or viral enhancer, in particular, of a virus which infects eukaryotes. Usually such enhancers occur in the 3' untranslated region (3'UTR) of a gene. Preferably (i) is an HBV or a CMV enhancer, for example an HBs Ag 3' UTR or a simian CMV immediate early gene 3' UTR. Preferably (i) comprises SEQ ID No. 8 or SEQ ID No. 9.

In general, the enhancer in the construct comprises sequences found in (i) which bind transcription components or regulatory proteins, for example transcription factors, or homologues of these sequences which bind the same components or proteins. Preferably these sequences are present in the enhancer in the same order and/or substantially the same relative spacing as in (i).

Generally a functional enhancer is one which enhances or increases expression of a polynucleotide, for example, a coding sequence, which is operably linked to the enhancer sequence. Typically a functional homologous variant (ii) or fragment (iii) has substantially the same activity (for example, enhancement of expression) as and/or complements the activity of the natural enhancer (i).

Enhancer activity may be assayed using an enhancer trap assay. Protocols are known in the art. A functional homologous variant (ii) or fragment (iii) preferably provides at least 50% of the enhancer activity shown by the natural enhancer in such as assay. Typically the activity is at least 60%, 70%, 80%, 90, 100% or more of the activity of the natural enhancer. In general, a functional variant (ii) or fragment (iii) is able to complement the activity of the natural enhancer (i) in the assay.

Enhancer utility may also be tested using the Comparative Expression Assay set out below. A test 3'UTR sequence is swapped into the base vector. A 3'UTR has utility if it does not abrogate expression but preferably increases expression in at least one but preferably two reference cell types compared to the base vectors in the assay. Preferably expression is increased by at least 5%, 10%, 20%, 30%, 40% or 50%. Preferred cell types are mammalian HEK293T, CHO, HeLa, BHK, 3T3 or COS cells. According to this assay, an homologous variant (ii) or fragment (iii) is functional if it allows greater than 50% of the expression improvement achieved by the natural enhancer sequence (i).

Additionally or alternatively, enhancer sequences may be tested for activity in the Comparative Immunogenicity Assay below. A 3'UTR is swapped into the base vector. A functional enhancer sequence provides antibody titres that are at least as high as or higher than those achieved by the base vector with at least one, preferably two antigens. Preferably the antibody titres are at least 5%, 10%, 20%, 30% or 40% higher than with the base vector. Preferred antigens are HBs Ag, HSV2gD and Flu-M2 antigens. An homologous variant (ii) or fragment (iii) is functional if it allows the highest antibody titre allowed by the natural enhancer sequence (i).

Suitable enhancer sequence can be obtained using standard cloning methods. For example, HBsAg 3'UTR sequence, or simian CMV immediate early gene 3'UTR sequence can be accessed at GenBank AF143308 and M16019. Primers can be designed based on this known sequence and used to isolate homologous sequences.

In a preferred embodiment, the nucleic acid construct comprises a heterologous polyA sequence, a heterologous leader sequence and a heterologous enhancer, all in operable linkage with the chimeric promoter, for efficient expression of an inserted coding sequence.

In a further aspect, the present invention also provides a nucleic acid construct comprising, or sometimes consisting essentially of:
(i) a promoter sequence
(ii) a non-translated leader sequence derived from HBV preS2 antigen sequence, HBV e-antigen sequence or HSV type 2 gD antigen sequence; and
(iii) a coding sequence operably linked to (i) and (ii)
wherein the coding sequence is heterologous to the non-translated leader sequence.

Typically the promoter sequence (i) is derived from a viral or eukaryotic promoter sequence. The promoter sequence may be a natural promoter sequence, a functional homologue of the natural sequence or a functional fragment of either. Suitable natural promoters include, for example, the hCMV immediate early promoter, Pseudorabies virus (PRV) promoter or Rous sarcoma virus (RSV) promoter. Preferably the natural promoter comprises SEQ ID NO: 52 or SEQ ID NO: 53.

An artificial promoter construct, such as the chimeric promoter described above, may be used, provided that the promoter is functional.

A functional promoter sequence is generally one which is able to cause (including initiate and regulate) transcription of an operably linked coding sequence in a suitable host cell.

A promoter sequence may be tested for promoter activity using a routine expression assay. A functional homologue or fragment of a natural promoter sequence typically provides at least 50%, for example, or least 60, 70, 80 or 90% of the expression provided by the natural sequence in such an assay.

The non-translated leader sequence-(ii) is as described above. Suitable coding sequences (iii) include those already described in relation to the chimeric promoter construct. However, in the present aspect of the invention, the coding sequence is heterologous to the non-translated leader sequence. The present construct typically includes a poly A sequence, which as already described, may be native to the coding sequence, or provided as a heterologous poly A sequence in the construct. Suitable poly A sequences have already been described. The construct may additionally include an enhancer sequence 3' of the coding sequence. Suitable enhancer sequences are described above in relation to the chimeric promoter construct.

In another aspect, the invention provides a nucleic acid construct comprising, or in some embodiments consisting essentially of:
(i) a promoter sequence;
(ii) a coding sequence operably linked to the promoter sequence (i) and;
(iii) an enhancer sequence 3' of and operably linked to the coding sequence (ii);
wherein the enhancer sequence (iii) is derived from a 3'UTR of an HBsAg sequence or a 3'UTR of a simian CMV immediate early gene sequence, and the coding sequence (ii) is heterologous to the enhancer sequence.

The construct may include a non-translated leader sequence such as the ones already described in relation to the chimeric promoter construct.

Typically the promoter sequence (i) is derived from a viral or eukaryotic promoter sequence. The promoter sequence may be a natural promoter sequence, a functional homologue of the natural sequence or a functional fragment of either. Suitable natural promoters include, for example, the hCMV immediate early promoter, Pseudorabies virus (PRV) promoter or Rous sarcoma virus (RSV) promoter. Preferably the natural promoter comprises SEQ ID NO: 52 or SEQ ID NO: 53.

An artificial promoter construct, such as the chimeric promoter described above, may be used, provided that the promoter is functional.

A functional promoter sequence is generally one which is able to cause (including initiate and regulate) transcription of an operably linked coding sequence in a suitable host cell.

A promoter sequence may be tested for promoter activity using a routine expression assay. Functional homologues or fragments of a natural promoter sequence typically provide at least 50%, for example, or least 60, 70, 80 or 90% or the expression provided by the natural sequence in such an assay.

Suitable coding sequences (ii) include those already mentioned in relation to the chimeric promoter construct. However, in the present aspect, the coding sequence is heterologous to the 3' enhancer sequence. The enhancer sequence (iii) of the construct is described above. The present construct also typically includes a poly A sequence. As in the case of the chimeric promoter construct, this poly A region may be native to the coding sequence (ii) or may be provided as a heterologous poly A component in the construct.

A construct according to any aspect of the present invention may comprise a signal peptide sequence. The signal peptide sequence is inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allow for secretion of the polypeptide via the Golgi apparatus.

A signal-peptide for use in the invention may comprise:
(i) a natural signal peptide sequence;
(ii) a homologous variant of (i) which retains signal peptide activity; or
(iii) a fragment of (i) or (ii) which retains signal peptide activity.

Sequence (i) may be for example human tissue plasminogen activator signal peptide (hTPAsp) (GenBank L00141), the aprotinin signal peptide (GenBank AAD13685), tobacco extensin signal peptide (GenBank JU0465), or chicken lysosyme signal peptide (GenBank AF410481).

A signal peptide, suitable for use in the present invention, is one which will enable the secretion of heterologous proteins. A functional signal peptide can be identified in an assay which compares the effect of a test signal peptide with the effect of a known signal peptide—e.g. human tissue plasminogen activator signal peptide (hTPAsP)— and with the effect of having no signal peptide. The Comparative Expression Assay set out below may be used but with the following modification. Secretion expression vectors are constructed containing the base vector with either the test signal peptide, hTPAsp or no signal peptide. Coding sequences for polypeptides devoid of their naturally occurring signal peptides are inserted into the vectors and the vectors transformed into reference host cells. Preferably cells are mammalian HEK293T, CHO, HeLa, BHK, 3T3 or COS cells. The cell media is analysed for polypeptide expression levels. A functional signal peptide enables polypeptide secretion at a higher level than a vector lacking a signal peptide with at least one, preferably two polypeptides. Typically, secretion is 5% higher, or more preferably 10% higher or more, for example 20 or 50% higher or more. Typically, secretion levels are comparable to those obtained using hTPAsp.

Allowing secretion of encoded protein outside of an expressing cell may have a number of advantages, in particular where the protein is an antigen. For example, increased antigen secretion could allow greater antigen uptake and response by immune cells (macrophages, Langehan's cells, B-cells, T-cells etc), enable the ability of antigen to reach the bloodstream and signal cells (cytokines), enable an antigen to find cellular ligands and effect a function (antibodies, toxins such as cholera toxin, E. coli LT) and participate in normal cellular biochemical processes (cellular receptors).

A nucleic acid construct of the invention may be in the form of a plasmid expression vector. The vector may then include additional elements, such as an origin of replication, or selector genes. Such elements are known in the art and can be included using standard techniques. In one embodiment, the plasmid vector has the sequence in SEQ ID NO:14. Alternatively, the construct may be included in a viral vector construct.

In some embodiments, the nucleic acid, construct of the invention may comprise two or more of the chimeric promoters defined herein. Thus, the construct may comprise a plurality of chimeric promoters and in particular the construct may have two, three, four, five or more chimeric promoters. The chimeric promoters will preferably be each separately operably linked to a cloning site for insertion of a coding sequence. Thus, the construct may express two, three, four, five or more more coding sequences. The coding sequences expressed may be any of those specified herein. In a preferred instance, the construct has two chimeric promoters with each having a coding sequence operably linked to them. In particular, the two promoters may be transcribed away from each other.

In particular, the constructs with two promoters may express the A and B subunits of an ADP-ribosylating bacterial toxin, including any of those mentioned herein and preferably an LTA and B subunit.

In cases where the construct has multiple chimeric promoters each may comprise, or be operably linked to, any of the sequences mentioned herein. In a particularly preferred instance, the heterologous intron of one or more of the promoters may be the rat insulin gene intron A sequence. One or more of the chimeric promoters may also preferably comprise the 5' UTR of HSV-2gB pre-S2. One or more of the promoters may comprise the poly adenylation sequence of the rat beta globin gene.

In a preferred case, the nucleic acid construct of the invention may comprise two chimeric promoter sequences, with each promoter sequence being operably linked to a cloning site which has a coding sequence inserted into it, where each chimeric promoter comprises
(a) a hCMV immediate early promoter sequence;
(b) exon 1 and at least a part of exon 2 of the hCMV major immediate early gene; and
(c) a heterologous intron provided in place of the intron A region of the hCMV major immediate early gene.
with the coding sequence operably linked to one chimeric promoter encoding a LTA subunit and the coding sequence linked to the other encoding an LTB subunit. The construct can therefore express both subunits. Preferably:
the heterologous intron of each promoter is the rat insulin gene intron A sequence;
the sequence encoding each LT subunit is operably linked to the 5' UTR of HBV pre-S2; and/or
each LT encoding sequence is operably linked to the rat beta globin gene polyadenylation sequence.

A polynucleotide construct of the invention may be substantially free of or associated with cells or with cellular material. It may be in substantially isolated form, or it may be in substantially purified form, in which case it will generally comprise at least 90% e.g at least 95%, 98% or 99% of the polynucleotide or dry mass in the preparation.

The present nucleic acid molecules may be delivered to suitable host cells, for expression of a polynucleotide in operable linkage with the promoter. Preferably the host cells are mammalian cells, in particular human cells. Suitable methods for delivery of nucleic acids to such cells are known in the art and include, for example, dextran mediated transfection, calcium phosphate precipitation, electroporation and direct microinjection into nucleii.

As described above, a nucleic acid coding sequence in a construct may encode a therapeutically relevant polypeptide. The present constructs may therefore be used for nucleic acid immunisation or gene therapy using standard gene delivery protocols. Suitable methods for gene delivery are known in the art, as discussed below. The nucleic acid molecules can be delivered either directly to a subject, or alternatively, delivered ex vivo to cells derived from the subject whereafter the cells are reimplanted in the subject.

For use in nucleic acid immunisation or gene therapy, the nucleic acid constructs may be formulated as conventional pharmaceutical preparations. This can be done using standard pharmaceutical formulation chemistries and methodologies, which are available to those skilled in the art. For example, compositions containing one or more nucleic acid sequences (e.g., present in a suitable vector form such as a DNA plasmid) can be combined with one or more pharmaceutically acceptable excipients or vehicles to provide a liquid preparation.

Auxiliary substances, such as wetting or emulsifying agents, pH buffering substances and the like, may be present in the excipient or vehicle. These excipients, vehicles and auxiliary substances are generally pharmaceutical agents which may be administered without undue toxicity and which, in the case of vaccine compositions will not induce an immune response in the individual receiving the composition. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the preparation will contain a pharmaceutically acceptable excipient that serves as a stabilizer, particularly for peptide, protein or other like molecules if they are to be included in the composition. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

Certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, e.g., Liposomes: A Practical Approach, (1990) RPC New Ed., IRL Press). Cationic lipid preparations are also well known vehicles for use in delivery of nucleic acid molecules. Suitable lipid preparations include DOTMA (N-[1-(2,3-dioleyloxy)propyl]-N,N, N-trimethylammonium chloride), available under the tradename LIPOFECTIN®, and DOTAP (1,2-bis(oleyloxy)-3-(trimethylammonio)propane), see, e.g., Felgner et al. (1987) Proc. Natl. Acad. Sci. USA 84:7413-7416; Malone et al. (1989) Proc. Natl. Acad. Sci. USA 86:6077-6081; U.S. Pat. Nos. 5,283,185 and 5,527,928, and International Publication Nos WO 90/11092, WO 91/15501 and WO 95/26356. These cationic lipids may preferably be used in association with a neutral lipid, for example DOPE (dioleyl, phosphatidylethanolamine). Still further transfection-facilitating compositions that can be added to the above lipid or liposome preparations include spermine derivatives (see, e.g., International Publication No. WO 93/18759) and membrane-permeabilizing compounds such as GALA, Gramicidine S and cationic bile salts (see, e.g., International Publication No. WO 93/19768).

Alternatively, the nucleic acid molecules of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycosides). See, e.g., Jeffery et al. (1993) *Pharm. Res.* 10:362-368. Other particulate systems and polymers can also be used, for example, polymers such as polylysine, polyarginine, polyornithine, spermine, spermidine, as well as conjugates of these molecules.

Once formulated the compositions can be delivered to a subject in vivo using a variety of known routes and techniques. For example, the liquid preparations can be provided as an injectable solution, suspension or emulsion and administered via parenteral, subcutaneous, intradermal, intramuscular, intravenous injection using a conventional needle and syringe, or using a liquid jet injection system. Liquid preparations can also be administered topically to skin or mucosal tissue, or provided as a finely divided spray suitable for respiratory or pulmonary administration. Other modes of administration include oral administration, suppositories, and active or passive transdermal delivery techniques.

Alternatively, the compositions can be administered ex vivo, for example delivery and reimplantation of transformed cells into a subject are known (e.g., dextran-mediated transfection, calcium phosphate precipitation, electroporation, and direct microinjection of into nuclei).

The compositions are administered to a subject in an amount that is compatible with the dosage formulation and that will be prophylactically and/or therapeutically effective. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed. For example, it is generally expected that an effective dose of the polynucleotide will fall within a range of about 0.001 to 1000 µg, more preferably 0.01 to 10.0 µg.

In one instance, a nucleic acid construct of the invention may be used in conjunction with another nucleic acid construct. In one case, the nucleic acid construct may be one of those described herein for the expression of an adjuvant and the other construct may be a construct encoding one or more antigens. In a preferred case, both constructs may employ the chimeric promoters of the invention.

In the case where one construct expresses an adjuvant and the other an antigen or antigens, the antigens may in particular be from HSV or Hepatitis virus (particularly Hepatitis B virus). The antigens may in particular be the HSV ICP0, ICP4, ICP 22 and/ICP 27 antigens and preferably all four. In cases where such antigens are expressed, the adjuvant construct will in particular express LTA and/or LTB and in particular both.

The two constructs may be administered separately, simultaneously or sequentially. The two may be administered in the same or different compositions. In particular, where one construct has an adjuvant effect the two will be delivered so that an adjuvant effect is seen, that is the immune response generated will be greater and/or for a longer period than if the adjuvant had not been administered with the antigen. In a preferred instance, the two constructs may be delivered in the same composition, preferably on the same carrier particles.

In a preferred embodiment, the nucleic acid constructs of the invention are delivered to target cells using a particle-mediated delivery technique. Particle mediated methods for delivering nucleic acid preparations are known in the art.

Particles for particle mediated delivery may be formed by coating the present nucleic acid molecules onto carrier particles (e.g., core carriers) using a variety of techniques known in the art. Carrier particles are selected from materials which have a suitable density in the range of particle sizes typically used for intracellular delivery from a particle-mediated delivery device. Typically carrier particles have a diameter of from 0.1 to 5 µm, for example 0.5 to 3 µm, preferably 1 to 2 µm. The optimum carrier particle size will, of course, depend on the diameter of the target cells. Alternatively, colloidal gold particles can be used wherein the coated colloidal gold is administered (e.g., injected) into tissue (e.g., skin or muscle) and subsequently taken-up by immune-competent cells.

Usually carrier particles are selected from inert metals. The metals are inert in that they are not physiologically active. For the purposes of the invention, tungsten, gold, platinum and iridium carrier particles can be used. Tungsten and gold particles are preferred. Tungsten particles are readily available in average sizes of 0.5 to 2.0 μm in diameter. Although such particles have optimal density for use in particle acceleration delivery methods, and allow highly efficient coating with DNA, tungsten may potentially be toxic to certain cell types. Gold particles or microcrystalline gold (e.g., gold powder A1570, available from Engelhard Corp., East Newark, N.J.) will also find use with the present methods. Gold particles provide uniformity in size (available from Alpha Chemicals in particle sizes of 1-3 μm, or available from Degussa, South Plainfield, N.J. in a range of particle sizes including 0.95 μm) and reduced toxicity. Microcrystalline gold provides a diverse particle size distribution, typically in the range of 0.1-5 μm. However, the irregular surface area of microcrystalline gold provides for highly efficient coating with nucleic acids.

A number of methods are known and have been described for coating or precipitating DNA or RNA onto gold or tungsten particles. Most such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in particular particle-mediated delivery instruments.

As an alternative, the polynucleotides of the invention can be formulated as a particulate composition. Formulation can be carried out using the above-described standard pharmaceutical formulation chemistries. For example, the polynucleotides can be combined with one or more pharmaceutically acceptable excipients or vehicles to provide a suitable composition. The formulated compositions are then prepared as particles using standard techniques such as by simple evaporation (air drying), vacuum drying, spray drying, freeze drying (lyophilisation), spray-freeze drying, spray coating, precipitation, supercritical fluid particle formulation, and the like. If desired, the resultant particles can be densified using the techniques described in commonly owned International Publication No. WO 97/48485, incorporated herein by reference.

These methods can be used to obtain nucleic acid particles having a size ranging from about 0.01 to about 250 μm, preferably about 10 to about 150 μm, and most preferably about 20 to about 60 μm; and a particle density ranging from about 0.1 to about 25 $g/cm^3$, and a bulk density of about 0.5 to about 3.0 $g/cm^3$, or greater.

Once formed, the particles comprising the nucleic acid molecules may be packaged in single unit dosages or multi-dose containers. Such containers may comprise an hermetically sealed container enclosing a suitable amount of the particles. The particles can be packaged as a sterile formulation, and the hermetically sealed container can thus be designed to preserve the sterility of the formulation until use in delivery to a subject. The containers are preferably adapted for direct use in a particle mediated delivery device. Typically such containers take the form of capsules, foil pouches, sachets, cassettes and the like. The particle delivery devices can also be provided in a preloaded condition containing a suitable dosage of the particles. The preloaded device may then also be prepackaged in a hermetically sealed container.

The container in which the particles are packaged can further be labelled to identify the composition and provide relevant dosage information. In addition, the container can be labelled with a notice in the form prescribed by a governmental agency, for example, the Food and Drug Administration, wherein the notice indicates approval by the agency under Federal Law of the manufacture, use or sale of the nucleic acid preparation contained therein for human administration.

Particle acceleration devices, suitable for particle-mediated delivery are known in the art. For example, current gene gun devices employ an explosive, electric or gaseous discharge to propel coated carrier particles towards target cells. The coated carrier particles can be releasably attached to a movable carrier sheet, or removably attached to a surface along which a gas stream passes, lifting the particles from the surface and accelerating them toward the target. An example of a gaseous discharge device is described in U.S. Pat. No. 5,204,253. An explosive-type device is described in U.S. Pat. No. 4,945,050. One example of an electric discharge apparatus suitable for use herein is described in U.S. Pat. No. 5,120,657. Another electric discharge apparatus is described in U.S. Pat. No. 5,149,655. The disclosure of all of these patents is incorporated herein by reference in their entireties.

Particles may also be administered using a needleless syringe device, such as those described in U.S. Pat. No. 5,630,796 to Bellhouse et al ("the POWDERJECT® needleless syringe device") and in International Publication Nos. WO 94/24263, WO 96/04947, WO 96/12513 and WO 96/20022, all of which are incorporated herein by reference.

Devices such as the one described in U.S. Pat. No. 5,630,796 may be provided as a pen-shaped instrument containing, in linear order moving from top to bottom, a gas cylinder, a particle cassette or package, and a supersonic nozzle with an associated silencer medium. The particles are provided within a suitable container, e.g. a cassette formed by two rupturable polymer membranes that are heat-sealed to a washer-shaped spacer to form a self-contained sealed unit. Membrane materials can be selected to achieve a specific mode of opening and burst pressure that dictate the conditions at which the supersonic flow is initiated.

In operation, the device is actuated to release the compressed gas from the cylinder into an expansion chamber within the device. The released gas contacts the particle cassette and, when sufficient pressure is built up, suddenly breaches the cassette membranes sweeping the particles into the supersonic nozzle for subsequent delivery. The nozzle is designed to achieve a specific gas velocity and flow pattern to deliver a quantity of particles to a target surface of predefined area. The silencer is used to attenuate the noise produced by the supersonic gas flow.

The delivery system described in International Publication No. WO 96/20022 also uses the energy of a compressed gas source to accelerate and deliver powdered compositions. However, it is distinguished from the system of U.S. Pat. No. 5,630,796 in its use of a shock wave instead of gas flow to accelerate the particles. More particularly, an instantaneous pressure rise provided by a shock wave generated behind a flexible dome strikes the back of the dome, causing a sudden eversion of the flexible dome in the direction of a target surface. This sudden eversion catapults a powdered composition (which is located on the outside of the dome) at a sufficient velocity, thus momentum, to penetrate target tissue, e.g., oral mucosal tissue. The powdered composition is released at the point of full dome eversion. The dome also serves to completely contain the high-pressure gas flow which therefore does not come into contact with the tissue. Because the gas is not released during this delivery operation, the system is inherently quiet. This design can be used in other enclosed or other wise sensitive applications for example, to deliver particles to minimally invasive surgical sites.

Particles may be delivered in vivo directly to a subject, or ex vivo to cells taken from a subject, the transformed cells then being reimplanted in the subject. For in vivo delivery, particle injection is typically subcutaneously, epidermally, intradermally, intramucosally (e.g. nasally, rectally and/or vaginally), intraperitoneally, intravenously, orally or intramuscularly. Preferably, delivery is to terminally differentiated cells; however, the particles can also be delivered to non-differentiated, or partially differentiated cells such as stem cells of blood and skin fibroblasts. Most preferably, delivery is to skin epidermal cells.

The particles are administered to a subject in a manner compatible with the dosage formulation and in an amount that will be prophylactically and/or therapeutically, effective. A "therapeutically effective amount" of the present particulate compositions will be sufficient to bring about treatment or prevention of disease or condition symptoms, and will fall in a relatively broad range that can be determined by routine trials. Generally the particles are delivered in an amount of from 0.001 to 1000 µg, more preferably 0.01 to 10.0 µg of nucleic acid per dose. However, the exact amount necessary will vary depending on the age and general condition of the individual being treated and the particular nucleotide sequence selected, as well as other factors. An appropriate effective amount can be readily determined through clinical testing. The "Physicians Desk Reference" and "Goodman and Gilman's The Pharmacological Basis of Therapeutics" are useful for the purpose of determining the amount needed.

Assays
Comparative Expression Assay

A suitable test for element utility determines the effect the element has on expression of a polypeptide. The basis of comparison for testing utility of the elements is a 'base vector', generally (unless otherwise noted) a plasmid with a hCMV promoter, hCMV exon 1, 9 bases of hCMV exon 2, the 5'UTR from HBV preS2 and the rabbit-β, globin_polyadenylation region, positioned to drive expression of a coding sequence. Typically, the base vector is pJV7384, PJV 7401, pJV 7450 or pJV 7533. Heterologous introns and 3'UTRs are added, or promoter sequences, exons, 5'UTRs and polyA sites are swapped into the base vectors to create test expression vectors. Thus functional variants or fragments can be tested.

The base vectors and test vectors are transformed into suitable host cells and the cells analysed for polypeptide expression levels. Preferably mammalian host cells are used. Suitable cells include mammalian HEK 293T, CHO, HeLa, BHK, 3T3 or COS cells.

Typically, a functional element causes expression which is comparable to the base vector, for example at least the same as or greater. Preferably expression is tested in more than one cell type and with more than one coding sequence.

Suitable experimental protocols are provided, for example, in Examples 1 to 13 below.

Comparative Immunogenicity Assay

Where the polypeptide to be expressed is an antigen, a further test may be carried out to identify functional or particularly preferred construct elements. In the assay, the effect of an element on immune response is determined after delivery of an expression vector to a test organism. Antibody levels against the antigen are the easiest way to judge immune response. Groups of mice are vaccinated with the base vectors or test vectors constructed as above. Sera is collected after an appropriate amount of time and analyzed for antibody levels.

This experiment is performed twice, and the antibody levels from all the groups in both experiments are plotted. Functional elements will give rise to at least as high as or higher antibody titres in both experiments for a particular antigen than the base vector. Preferably, the result will be seen with more than one antigen to demonstrate the breadth of utility of the element(s) in that expression panel.

Suitable experimental protocols are provided for example, in Example 14 below.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Methods
Standard PCR Conditions

The standard PCR conditions used for the construction of vectors were as follows: 1×PCR core buffer w/1.5 mM MgCl2 (Promega Corporation, Madison, Wis.), 0.400 µM each of each primer, 200 µM of each dNTP (USB, Inc, Cleveland, Ohio), 2.5µ Taq polymerase (Promega Corporation, Madison, Wis.), 1.0 ng template DNA, water to 100 µl, and a mineral oil (Aldrich Chemical, Inc, Milwaukee, Wis.) overlay. The PTC-200 thermocycler (MJ Research, Inc, Waltham, Mass.) was programmed to run the following routine: 4'@95° C., 30 cycles of (1'@95° C./1'15"@55° C./1'@72° C.), 10'@72° C., 4° C. hold). The amplification products were removed from the PCR reaction by using the QIAquickâPCR Purification Kit (Qiagen Inc, Valencia, Calif.) prior to cutting with restriction enzymes (New England Biolabs, Beverly, Mass.).

All PCR products were sequenced after cloning to ensure fidelity of the amplification.

Example 1

Construction of Hepatitis B Virus Surface Antigen (HBsAg) Vector Panels

A number of plasmid expression vectors were constructed for expression of HBsAg.

Starting Materials (i) pWRG7128 (Roy, M, et al. *Vaccine* (2001) 19: 764-778), which contains the hCMV immediate early promoter sequence, the first exon, first intron, and a partial second exon of the hCMV major immediate early gene, the HBsAg coding sequence with flanking regions (HBV preS2 5'UTR derived sequence and 3' posttranscriptional response element) and the bovine growth hormone polyadenylation region (BGHpA)

(ii) pJV7284, a derivative of pWRG7128 that exchanges the rabbit β globin polyadenylation region (RBGpA) for BGHpA.

(a) pJV7384 (CMV(No Intron), HBV preS2 5'UTR and RBGpA)

pWRG7128 was PCR'd with JF93 (SEQ ID NO:15) and F110 (SEQ ID NO:16) using standard conditions and cut with Sal1 and BamH1 to isolate an insert fragment containing the CMV promoter, exon 1 and part of the exon 2 sequence. pAM6 (ATCC, Mannassas, Va.) was cut with BamH1 and BstX1 to isolate an insert fragment that contained the 5'-UTR of HBsAg, and roughly 70% of the HBsAg coding region. pJV7284 was cut with Sal1 and BstX1 to generate a vector fragment into which the two insert fragments were ligated, resulting in pJV7293.

pWRG7128 was PCR'd with primers GW1 (SEQ ID NO:17) and JF254 (SEQ ID NO:18) and cut with BstX1 and Bgl2 to isolate an insert fragment that contained the 3'-end of the HBsAg coding region. pJV7293 was cut with BstX1 and Bgl2 to generate a vector fragment into which the insert fragment was ligated, resulting in vector pJV7384.

(b) pJV7382 (CMV(No Intron), HBsAg 3'UTR, HBV preS2 5'UTR and RBGpA)

pJV7293 was cut with Xho1 and Xba1 to generate an insert fragment containing the CMV promoter/exons and the 5'-UTR with 5'-end of the HBsAg coding sequence. pWRG7128 was cut with Xba1 and Bcl1 to generate an insert fragment containing the majority of the HBsAg coding sequence and the 3'-UTR. pJV7284 was cut with Xho1 and Bgl2 to generate a vector fragment into which the two insert fragments were ligated, resulting in pJV7382.

(c) pJV7389 (CMV (RIA); HBsAg 3'UTR, HBV preS2 5'UTR and RBGpA)

The rat insulin intron A (RIA) was PCR'd out of plasmid p5'rIns (unknown origin) with primers GW150 (SEQ ID NO:19) and JF255 (SEQ ID NO:20). The PCR product was cut with BamH1 and inserted into BamH1 linearized pJV7382, resulting in pJV7389.

(d) pJV7387 (CMV(RIA), HBV preS2 5'UTR and RBGpA)

pJV7384 was cut with BstX1 and EcoR1 to generate an insert fragment containing the 3' end of the HBsAg coding region and RBGpA. pJV7389 was cut with BstX1 and EcoR1 to generate a vector fragment into which the insert fragment was ligated, resulting in pJV7387.

Example 2

Construction of Herpes Simplex Virus Glycoprotein D Antigen (HSVgD) Vector Panels A number of plasmid expression vectors were constructed for expression of HSVgD.

Starting Materials (a) pJV7334, a derivative of pWRG7284 (pJV 7284) that replaces the HBsAg coding sequence with an in-frame Nhe1 directly downstream of the ATG start codon, followed by a stuffer fragment with a BamH1 immediately 5' of the HBV Enh (b) pWRG7202, a derivative of pGem3Z (Promega) with a stuffer fragment that allows the fusion of a coding sequence to the human tissue plasminogen activator (TPA) signal peptide downstream of a Nhe1 site.

(a) pJV7392(CMV(Native Intron), HBsAg 3'UTR, HBsAg 5'UTR and RBGpA)

The coding region for HSV2 gD was PCR'd out of a viral DNA stock (Advanced Biotech, Inc, Columbia, Md.) using primers DS1 (SEQ ID NO:21) and DA1 (SEQ ID NO:22) and was cut with Nhe1 and EcoR1 to generate an insert fragment. pWRG7202 was cut with Nhe1 and EcoR1 to generate a vector fragment into which the insert fragment was ligated, resulting in pJV7391.

pJV7391 was cut with Nhe1 and Bgl2 to generate an insert fragment containing the HSV2 gD coding sequence. pJV7334 was cut with Nhe1 and BamH1 to generate a vector fragment into which the insert fragment was ligated, resulting in pJV7392. This vector consists of the following expression elements: the hCMV immediate early promoter sequence, the first exon, first intron, and a partial second exon of the hCMV major immediate early gene, the 5'-UTR from HBsAg, the coding sequence for HSV2' gD gene, the 3'-UTR from HBsAg, and RBGpA.

(b) pJV7399 (CMV(No Intron), HBsAg 3'UTR HBsAg 5'UTR and RBGpA)

An intronless version of pJV7392 was constructed as follows. pJV7384 was cut with Hind3 and Nde1 to isolate an insert fragment containing the 5' ends of the kanamycin resistance gene and the CMV promoter. pJV7384 was cut with Nde1 and Ssp1 to isolate an insert fragment containing the 3' end of the CMV promoter, the CMV exon ½ and 5' end of the 5'-UTR from HBsAg. These insert fragments were inserted into pJV7392 from which the Hind3-Ssp1 fragment was removed, resulting in pJV7399.

(c) pJV7400 (CMV(RIA), HBsAg 3'UTR, HBsAg 5'UTR and RBGpA)

A RIA version of pJV7392 was constructed as follows. pJV7384 was cut with Hind3 and Nde1 to isolate an insert fragment containing the 5' ends of the kanamycin resistance gene and CMV promoter. pJV7387 was cut with Nde1 and Ssp1 to isolate an insert fragment containing the 3' end of the CMV promoter, the CMV exon ½(partial), RIA, and 5' end of the 5'-UTR from HBsAg. These insert fragments were inserted into pJV7392 from which the Hind3-Ssp1 fragment was removed, resulting in pJV7400.

(d) pJV7401 (CMV(No Intron), HBsAg 5'UTR and RBGpA)

A 3'-UTR-less version of pJV7399 was constructed as follows. pJV7391 was cut with Bsp1201 and Bgl2 to isolate an insert fragment containing the 3' end of the HSV2 gD gene. pJV7284 was cut with Bgl2 and EcoR1 to isolate the RBGpA signal. These insert fragments were inserted into pJV7399 from which the Bsp1201-EcoR1 fragment was removed, resulting in pJV7401.

(e) pJV7402 (CMV(RIA), HBsAg 5'UTR and RBGpA)

A 3'-UTR-less version of pJV7400 was constructed as follows. pJV7391 was cut with Bsp1201 and Bgl2 to isolate an insert fragment containing the 3' end of the HSV2 gD gene. pJV7284 was cut with Bgl2 and EcoR1 to isolate the RBGpA signal. These insert fragments were ligated into pJV7400 from which the Bsp1201-EcoR1 fragment was removed, resulting in pJV7402.

Example 3

Construction of Flu M2 Antigen Vector Panels (a) pJV7450 (CMV(No Intron), HBsAg 5'UTR and RBGpA)

A coding region for Flu M2 was PCR'd out of plasmid pFL-M2 (Joel Haynes, PJV) using primers JF301 (SEQ ID NO:23) and JF302 (SEQ ID NO:24) and was cut with Nhe1 and Bgl2 to generate an insert fragment. pJV7401 was cut with Nhe1 and Bgl2 to generate a vector fragment into which the insert fragment was ligated, resulting in pJV7450.

(b) pJV7452 (CMV(No Intron), HBsAg 3'UTR, HBsAg 5'UTR and RBGpA).

A 3'UTR fragment was PCR'd out of pJV7389 with primers JF84 (SEQ ID NO:25) and JF225 (SEQ ID NO:26) was cut with Bsp1201, filled with T4 DNA polymerase, and linkered with Bgl2 linkers (cat#1036, New England Biolabs). The fragment was then cut with Bgl2 and EcoR1 to isolate an insert fragment containing the 3'UTR of HBsAg and the RBGpA region. pJV7450 was cut with Bgl2 and EcoR1 to generate a vector fragment into which the insert fragment was ligated, resulting in pJV7452

(c) pJV7458 (CMV(RIA) HBsAg 5' UTR and RBGpA)

A version of pJV7450 containing the RIA was constructed as follows: pJV7389 was cut with BamH1 to isolate a RIA containing insert fragment. pJV7450 was cut with BamH1 to generate a vector fragment into which the insert fragment was ligated, resulting in pJV7458.

(d) pJV7468 (CMV(RIA), HBsAg 3'UTR, HBsAg 5'UTR and RBGpA)

A version of pJV7458 containing the 3'UTR of HBsAg was constructed as follows: pJV7452 was cut with Bgl2 and EcoR1 to produce an insert fragment containing the HBsAg 3'UTR and RBGpA. pJV7458 was cut with Bgl2 and EcoR1 to generate a vector fragment into which the insert fragment was ligated, resulting in pJV7468.

Example 4

Construction of Beta-Gal Vector Panels (a) pJV7488 (CMV(No Intron), HBsAg 3'UTR, HBsAg 5'UTR and RBGpA)

CMV-beta (Clontech) was PCRed with primers JF335 (SEQ ID NO:27) and JF336 (SEQ ID NO:28) and cut with Nhe1 and Bgl2 to isolate an insert fragment coding for beta-galactosidase. pJV7452 was cut with Nhe1 and Bgl2 to generate a vector fragment into which the insert fragment was ligated, resulting in pJV7488.

(b) pJV7533 (CMV(No Intron), HBsAg 5'UTR and RBGpA)

pJV7450 was cut with Bgl2 and EcoR1 to isolate an insert fragment containing the RBGpA. pJV7488 was cut with Bgl2 and EcoR1 to generate a vector fragment into which the insert fragment was ligated, resulting in pJV7533.

(c) pJV7551 (CMV(RIA/NheI), HBsAg 3'UTR, HBsAg 5'UTR and RBGpA)

pJV7530 (see Example 5) was cut with Xho1 and BamH1 to isolate an insert fragment containing the CMV promoter through RIA. pJV7488 was cut with Xho1 and BamH1 to generate a vector fragment into which the insert fragment was ligated, resulting in pJV7551.

(d) pJV7552(CMV(RIA/NheI), HBsAg 5'UTR and RBGpA)

pJV7530 was cut with Xho1 and BamH1 to isolate an insert fragment containing the CMV promoter through RIA. pJV7533 was cut with Xho1 and BamH1 to generate a vector fragment into which the insert fragment was ligated, resulting in pJV7552.

Example 5

Construction of pJV Expression (pJV7563)

(a) pJV7496 pJV7389 was PCR'd with primers JF357 (SEQ ID NO:29) and JF365 (SEQ ID NO: 30), treated with T4 DNA polymerase to blunt the ends, and cut with Sal1 to isolate an insert fragment coding for kanamycin resistance. pJV7389 was cut with Ava1, treated with T4 DNA polymerase to blunt the ends, and cut with Sal1 to isolate a vector fragment into which the insert fragment was ligated, resulting in pJV7496.

(b) pJV7530 pJV7389 was PCR'd with primers JF393 (SEQ ID NO:31) and JF406 (SEQ ID NO:32) and cut with Bgl2 and BamH1 to isolate an insert fragment containing the RIA devoid of an internal Nhe1 site. pJV7496 was cut with BamH1 to prepare a vector fragment into which the insert fragment was ligated, resulting in pJV7530.

(c) pJV7549 pJV7468 was cut with BamH1 and EcoR5 to isolate an insert fragment containing M2 and part of the HBV 3'ENH. pJV7530 was cut with BamH1 and EcoR5 to prepare a vector fragment into which the insert fragment was ligated, resulting in pJV7549.

(d) pJV7563

Figure 12:
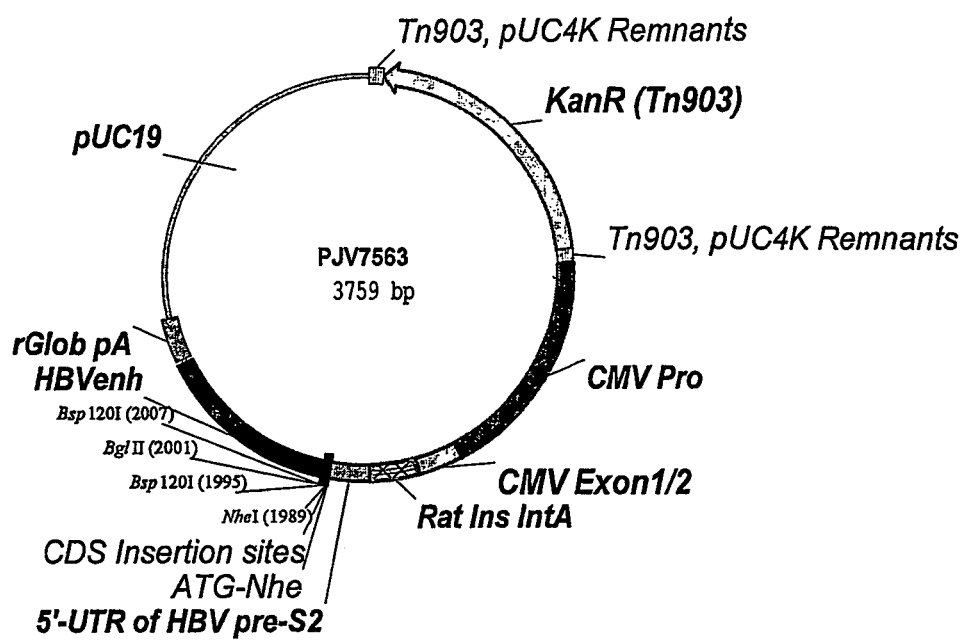
FIG. 12 is a diagrammatic representation of pJV7563.

Primers JF256 (SEQ ID NO:33) and JF257 (SEQ ID NO:34) were annealed to prepare an insert fragment consisting of a multiple cloning site. pJV7549 was cut Nhe1 and Bgl2 to prepare a vector fragment into which the insert fragment was ligated, resulting in pJV7563. A pJV7563 plasmid map is provided in FIG. 12. The base composition for the pJV7563 plasmid is provided in FIG. 13. The components and their position in the plasmid pJV7563 are as follows:

- 1-44 Transposon 903 sequences
- 45-860 Kanamycin resistance coding sequence from Transposon 903
- 861-896 Transposon 903 sequences
- 897-902 Sal1 site
- 903-1587 CMV promoter
- 1588-1718 untranslated leader sequence from the immediate-early gene of CMV
- 1719-1724 Fusion of BamH1 and BgIII restriction enzymes
- 1725-1857 Rat insulin intron A
- 1858-1863 BamH1 site
- 1864-1984 HBV surface antigen 5'-untranslated leader
- 1985-1993 Synthetic start codon/Nhe1 cloning site
- 1994-2011 Synthetic cloning sites
- 2012-2544 HBV enhancer
- 2545-2555 Old vector sequence. No hits against NCBI databases
- 2556-2686 Rabbit beta-globin polyadenylation region
- 2687-3759 pUC19 vector sequence Example 6

Construction of Signal Peptide Expression Panels Using Human Secreted Alkaline Phosphatse (SEAP) and Human IgG Fc Fragment (hFc) as Model Antigens (i) pJV7507 (hTPAsp and SEAP)

pSEAP-Basic (Clontech) was PCR'd with primers JF320 (SEQ ID NO:35) and JF321 (SEQ ID NO:36) then cut with Nhe1 and Bgl2 to isolate an insert fragment consisting of the human SEAP fragment. pJV7079 (Macklin, et.al.) was cut with Nhe1 and Bgl2 to prepare a vector fragment into which the insert fragment was ligated, resulting in pJV7507.

(ii) pJV7508 (hTPAsp and hFc)

Human DNA was PCR'd with primers JF386 (SEQ ID NO:37) and FcAS (SEQ ID NO:38) then cut with Nhe1 and Bgl2 to isolate an insert fragment consisting of the human IgG Fc fragment. pJV7079 was cut with Nhe1 and Bgl2 to prepare a vector fragment into which the insert fragment was ligated, resulting in pJV7508.

(iii) Preparation of Aprotinin Signal Peptide Coding Sequence

Synthetic oligo JF354 (SEQ ID NO:39) was PCR'd with primers JF355 (SEQ ID NO:40) and JF356 (SEQ ID NO:41) to generate the coding sequence for the aprotinin signal peptide.

(iv) Preparation of Tobacco Extensin Signal Peptide Coding Sequence

Synthetic oligo JF348 (SEQ ID NO:42) was PCR'd with primers JF349 (SEQ ID NO:43) and JF350 (SEQ ID NO:44) to generate the coding sequence for the tobacco extensin signal peptide.

(v) Preparation of Chicken Lysozyme Signal Peptide Coding Sequence

Synthetic oligo JF351 (SEQ ID NO:45) was PCR'd with primers JF352 (SEQ ID NO:46) and JF353 (SEQ ID NO:47) to generate the coding sequence for the chicken lysozyme signal peptide.

(a) Flu M2 Antigen Signal Peptide Panels pJV7499 (CMV(no intron), HBsAg5'UTR, RBGpA. aprotinin s.p.)

pJV7497 (CMV(no intron), HBsAg5'UTR, RBGpA, tobacco extensin s.p.)

pJV7500 (CMV(no intron), HBsAg5'UTR, RBGpA, chicken lysosyme s.p.)

Coding sequences for the signal peptides were cut with Spe1 and Nhe1 to isolate insert fragments. pJV7450 was cut with Nhe1 to prepare a vector fragment into which the insert fragments were ligated, resulting in pJV7499 (aprotinin), pJV7497 (tobacco extensin), and pJV7500 (chicken lysozyme).

(b) SEAP Signal Peptide Panels pJV7513 (CMV(no intron), HBsAg5'UTR, RBGpA, aprotinin s.p.)

pJV7512 (CMV(no intron), HBsAg5'UTR, RBGpA, tobacco extensin sp.)

pJV7510 (CMV(no intron), HBsAg5'UTR, RBGpA, chicken lysosyme s.p.)

pJV7499; 7497, and 7500 were cut with Xho1 and Nhe1 to isolate an insert fragment consisting of the CMV promoter through the signal peptide coding sequence of the plasmids. PJV7507 was cut with Xho1 and Nhe1 to prepare a vector fragment into which the insert fragments were ligated, resulting in pJV7513 (aprotinin), pJV7512 (tobacco-extensin), and pJV7510 (chicken lysozyme).

(c) hFc Signal Peptide Panels pJV7524 (CMV(no intron), HBsAg5'UTR, RBGpA, aprotinin s.p.)

pJV7525 (CMV(no intron), HBsAg5'UTR, RBGpA, tobacco extensin s.p.)

pJV7526 (CMV(no intron), HBsAg5'UTR, RBGpA, chicken lysosyme signal peptide)

pJV7499, 7497, and 7500 were cut with Xho1 and Nhe1 to isolate an insert fragment consisting of the CMV promoter through the signal peptide coding sequence of the plasmids. pJV7508 was cut with Xho1 and Nhe1 to prepare a vector fragment into which the insert fragments were ligated, resulting in pJV7524 (aprotinin), pJV7525 (tobacco extensin), and pJV7526 (chicken lysozyme).

Example 7

Construction of Human Secreted Alkaline Phosphatase (SEAP) Panels (a) PJV7531 (CMV(No Intron), HBsAg5'UTR, RBGpA, Chicken Lysosyme s.p.)

pJV7510 was cut with Sal1 and Bgl2 to isolate an insert fragment containing the CMV promoter through lysozyme signal peptide. pJV7450 was cut with Sal1 and Bgl2 to generate a vector fragment into which the insert fragment was ligated, resulting in pJV7531.

(b) pJV7554 (CMV(RIA/NheI), HBsAg5'UTR, RBGpA, Chicken Lysosyme s.p.)

pJV7530 was cut with Xho1 and BamH1 to isolate an insert fragment containing the CMV promoter through RIA. pJV7531 was cut with Xho1 and BamH1 to generate a vector fragment into which the insert fragment was ligated, resulting in pJV7554.

(c) pJV7568 (CMV(No Intron), HBsAg 3'UTR, HBsAg5'UTR, RBGpA, Chicken Lysosyme s.p.)

pJV7563 was cut with Bgl2 and EcoR1 to isolate an insert fragment containing the HBV 3'-UTR and RBGpA. pJV7531 was cut with Bgl2 and EcoR1 to generate a vector fragment into which the insert fragment was ligated, resulting in pJV7568.

(d) PJV7572 (CMV(RIA/NheI), HBsAg 3'UTR, HBsAg5'UTR, RBGpA, Chicken Lysosyme s.p.)

pJV7563 was cut with Bgl2 and EcoR1 to isolate an insert fragment containing the HBV 3'UTR and RBGpA. pJV7554 was cut with Bgl2 and EcoR1 to generate a vector fragment into which the insert fragment was ligated, resulting in pJV7572.

Example 8

Construction of Beta-Gal and HBsAg Vectors Using the Chicken Keratin and Chicken Cardiac Actin Introns (a) pJV7557 (Beta-gal, CMV(cA intron), HBsAg3'UTR, HBsAg5'UTR and RBGpA)

Chicken DNA was PCR'd with primers JF430 (SEQ ID NO:48) and JF442 (SEQ ID NO:49) and cut with Bgl2 and BamH1 to isolate an insert fragment consisting of the intron and flanking exon sequences from chicken cardiac actin. pJV7488 was cut with BamH1 to prepare a vector fragment into which the insert fragment was ligated, resulting in pJV7557.

(b) PJV7558 (Beta-gal, CMV(cK Intron), HBsAg3'UTR, HBsAg5'UTR and RBGpA)

Chicken DNA was PCR'd with primers JF421 (SEQ ID NO:50) and JF444 (SEQ ID NO:51) and cut with Bgl2 and BamH1 to isolate an insert fragment consisting of the intron and flanking exon sequences from the chicken keratin gene. pJV7488 was cut with BamH1 to prepare a vector fragment into which the insert fragment was ligated, resulting in pJV7558.

(c) pJV7578 (HBsAg, CMV(cA intron), HBsAg3'UTR, HBsAg5'UTR and RBGpA)

pJV7557 was cut with Sal1 and BamH1 to isolate an insert fragment consisting of the CMV promoter through intron regions. pJV7496 was cut with Sal1 and BamH1 to prepare a vector fragment into which the insert fragment was ligated, resulting in pJV7558.

(d) PJV7579 (HBsAg, CMV(cK Intron), HBsAg3'UTR, HBsAg5'UTR and RBGpA)

pJV7558 was cut with Sal1 and BamH1 to isolate an insert fragment consisting of the CMV promoter through intron regions. pJV7496 was cut with Sal1 and BamH1 to prepare a vector fragment into which the insert fragment was ligated, resulting in pJV7579.

Example 9

In-Vitro Analysis of Antigen Expression by HBsAg Vector Panels

On day one, SCC15 (ATCC) or B16 (origin unknown, versions available at ATCC) cells were plated on 6 well tissue culture plates at 20-40% confluency, and allowed to grow overnight in an incubator. The host cells were propagated in media recommended by ATCC.

On day two, the transfection reaction was performed. For each vector to be tested, 20 µl of LIPOFECTIN® reagent (Life Technologies Inc., Grand Island, N.Y.) was added to 180 µl of OPTIMEM® media (Life Technologies Inc., Grand Island, N.Y.), and allowed to incubate at room temperature for 45 minutes. For each" vector to be tested, 2 µg of vector was mixed into 200 µg of OPTIMEM® media at 40 minutes. At 45 minutes, the vector and LIPOFECTIN® reagent solutions were mixed together and allowed to sit at room temperature for an additional 10 minutes. During this final incubation, the plated host cells were removed from the incubator and washed twice with OPTIMEM® media. At 10 minutes, 1.6 ml of OPTIMEM® media was added to the LIPOFECTIN® reagent/vector mix, and 1 ml of the resultant mix was added to each of two cell wells. The host cells were returned to the incubator and allowed to sit undisturbed for 5 hours, at which point the LIPOFECTIN® reagent/vector mix was removed and replaced by standard cell maintenance media.

At 18 to 24 hours after the media change, from 50 to 100 µl of cell maintenance media was removed from the tissue culture plates and analyzed for antigen expression by placing the samples into reactions vessels provided in the AUSZYME® Monoclonal Diagnostic Kit (Abbott Laboratories, Abbott Park, Ill.). The volume of the test samples was brought to a volume of 200 µl with PBS, then 50 µl of conjugate and a reaction bead were added to each sample. The vessel is incubated for 80 minutes at 40° C., after which the wells were washed clean of all liquid reaction components. The beads were transferred to new tubes after which 300 µl of color development buffer was added. At 30 minutes, the color development reaction was stopped by the addition of 1M sulfuric acid, and the absorbance of the reaction was measured at 490 nm. The data shown in FIG. 1 is the average absorbance readings of the duplicate wells from two experiments.

Figure 2:
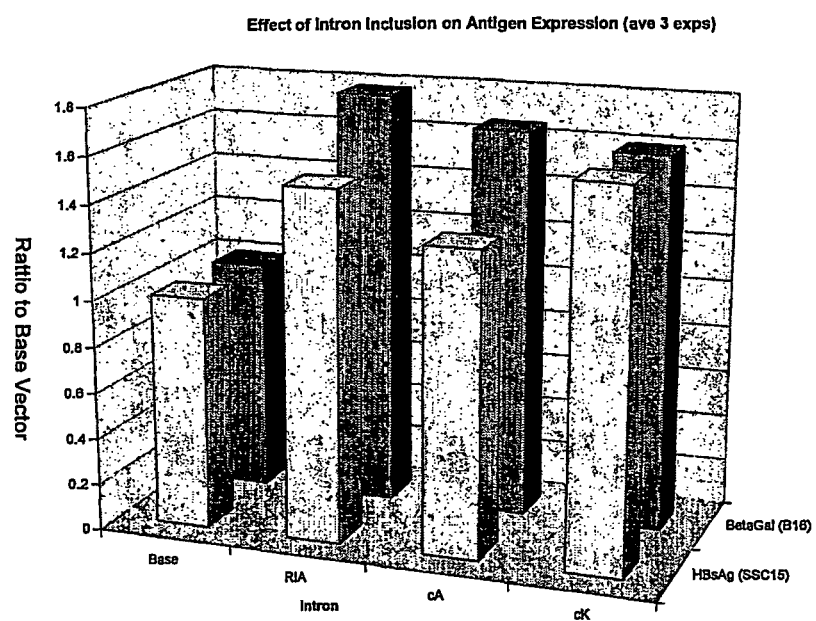
FIG. 2 shows the effect of intron inclusion on expression of HBsAg in SCC15 cells and of beta-gal in B16 cells (average of three expts).

As shown in FIG. 1, the addition of RIA, the HBV 3'UTR or both elements to a base vector (CMV promoter, axon and polyadenylation region) increased the expression of HBsAg in SCC15 cells. As shown in FIG. 2, the addition of either the chicken keratin or the chicken cardiac actin intron to a base vector (CMV promoter, exon, HBV 3'UTR and polyadenylation region) increased expression of HBsAg in SCC15 cells.

Example 10

In-Vitro Analysis of Antigen Expression by Beta-Gal Vector Panels

SSC-15 or B16 host cells were transfected as described in Example 9.

At eighteen to forty hours after, the media change, the media supernatants were removed and the cells were washed with PBS. After removal of the wash, the cells were lysed by incubating the cells in 500 µl lysis buffer (50 mM NaPO$_4$, 0.1% Triton X-100, pH 7) for 5 minutes, followed by physically scraping the cells off the plastic dish. The lysates were microfuged for two minutes to remove cell debris, and 10 to 25 µl of the cleared lysate were added to 500 µl of reaction buffer (80 ug/ml o-nitrophenyl galactopyranoside, 50 mM NaPO$_4$, pH 7) and incubated at 37° C. for 10 to 20 minutes. The reaction was stopped by the addition of 500 µl of 1M Na$_2$CO$_3$ and read at 405 nm. Data is presented as the ratio of the expression of enhanced (containing an intron, HBVenh, or both) vector to a base vector.

Figure 3:
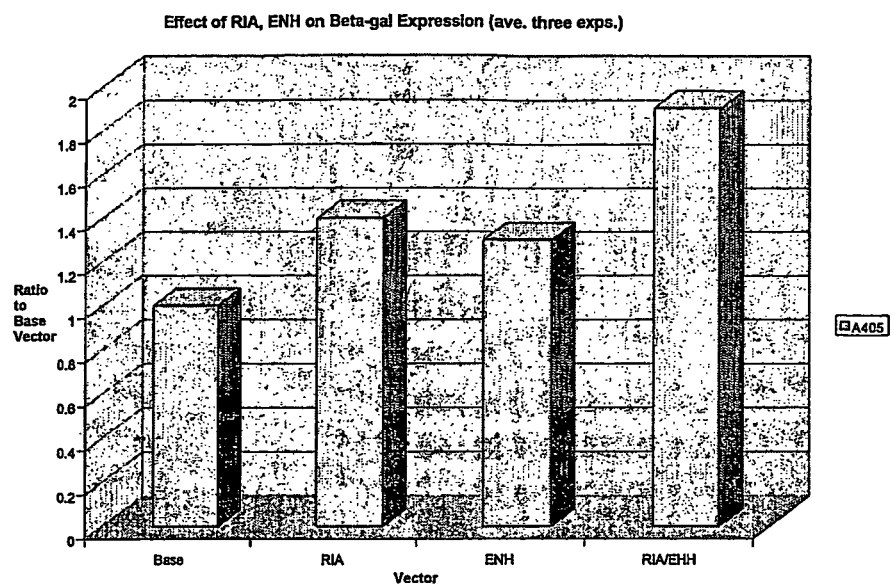
FIG. 3 shows the effect of rat insulin intron A and HBV3'UTR on expression of beta-gal in SCC15 cells (average of three expts).

The addition of RIA, the HBV 3'UTR or both elements to a base vector (CMV promoter, exon and polyadenylation region) increased the expression of beta-gal in both cell lines. The results for SCC15 cells are shown in FIG. 3. Addition of either the chicken keratin or the chicken cardiac actin intron to a base vector (CMV promoter, exon, the HBV 3'UTR and polyadenylation region) increased the expression of beta-gal in both cell lines. Results for B16 cells are shown in FIG. 2.

Example 11

In-Vitro Analysis of Antigen Expression by HSV gd Vector Panel

SCC15 or B16 host cells were transfected as described in Example 9. Eighteen hours post transfection, plates were placed on ice for 15 minutes. Each well was then washed with 2 ml of PBS (Biowhittaker, Walkerville, Md.). Cells were fixed with 0.05% gluteraldehyde (Polysciences Inc, Warrington, Pa.) diluted in PBS and incubated for 30 minutes at room temperature. All subsequent incubations lasted 1 hour at room temperature and washes between each incubation were as stated above. The plates were blocked with 2 ml of 5% dry milk (Bio Rad Laboratories, Melville, N.Y.) in PBS. Incubations with 1 ml of a 1:1000 dilution of anti-gD monoclonal (ABI, Columbia, Md.) in 2% dry milk/PBS 0.05% TWEEN®-20 polysorbate surfactant (Sigma, St. Louis, Mo.) and 1 ml of a 1:2500 dilution of goat anti-mouse HRP (KPL, Gaithersburg, Md.) in PBS/0.1% TWEEN®-20 polysorbate surfactant followed. Color was developed using 1 ml of TMB microwell substrate (BioFX, Owings Mills, Md.). The reactions were stopped with 1M H$_2$SO$_4$, the liquid was transferred to plastic cuvettes and the optical density read at 450 nm. Data is presented as the ratio of the expression of enhanced (containing an intron, HBVenh, or both) vector to a base vector.

Figure 4:
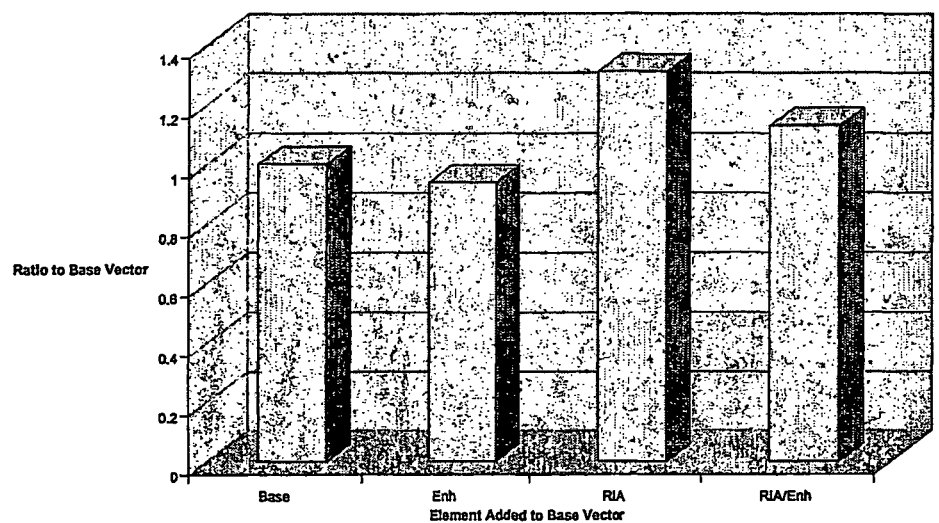
FIG. 4 shows the effect of rat insulin intron A and HBV3'UTR on expression of HSVgD in SCC15 cells (average of three expts).

Addition of RIA with or without the HBV 3'UTR to a base vector (CMV promoter, exon and polyadenylation region) increased the expression of HSV gD in both cell lines. Results for SC15 cells are shown in FIG. 4.

Example 12

In-Vitro Analysis of Antigen Expression by SEAP Vector Panels

SCC15 or B16 host cells were transfected as described in Example 9. At eighteen to forty hours after the media change, the media supernatants were removed and heated at 70° C. for 30 minutes. 10 to 25 µl of the heat-inactivated supernatants were incubated for 5 minutes with $\frac{1}{10}^{th}$ volume of 100 mM I-homoarginine. 500 µl of alkaline phosphatase reaction buffer (cat #172-1063, Bio-Rad, prepared according to instructions) were added to the lysates and incubated at 37° C. for 10 to 20 minutes. The reaction was stopped by the addition of 500 µl of 1M NaOH and read at 405 nm. Data is presented as the ratio of the expression of enhanced (containing an intron, HBVenh, or both) vector to a base vector, or the ratio of the expression of the experimental signal peptides to the human TPA signal peptide vector.

Figure 5:
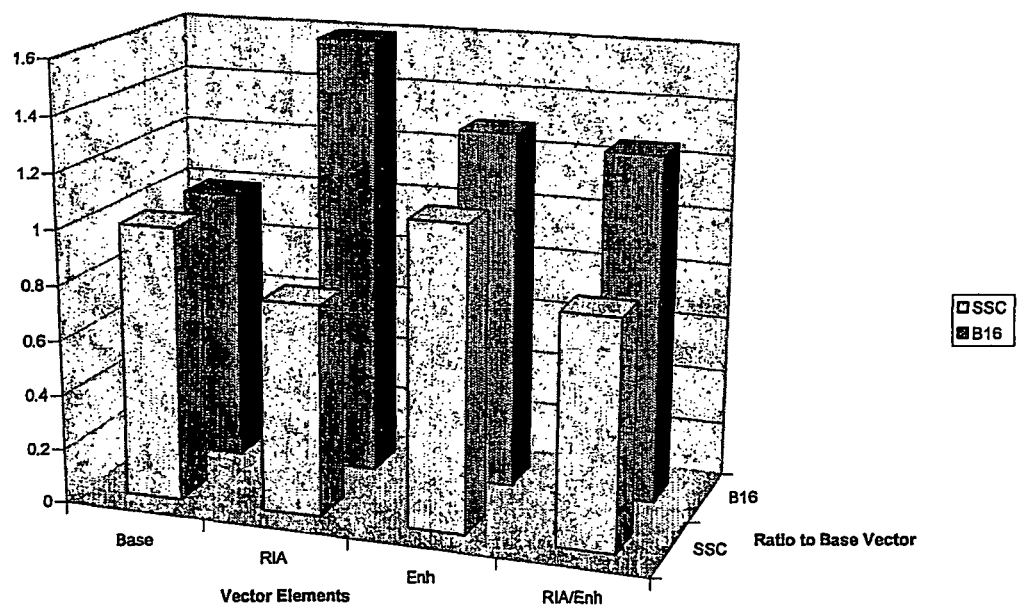
FIG. 5 shows the effect of rat insulin intron A and HBV3'UTR on expression of SEAP in SCC15 and B16 cells (three repetitions per cell line).

As shown in FIG. 5, the addition of RIA, the HBV 3'UTR or both elements to a base vector (CMV promoter, exon and polyadenylation region) increased the expression of SEAP in B16 cells. Unexpectedly, only the addition of the HBV 3'UTR to a base vector (CMV promoter, exon and polyadenylation region) increased the expression of SEAP in SCC15 cells.

Figure 6:
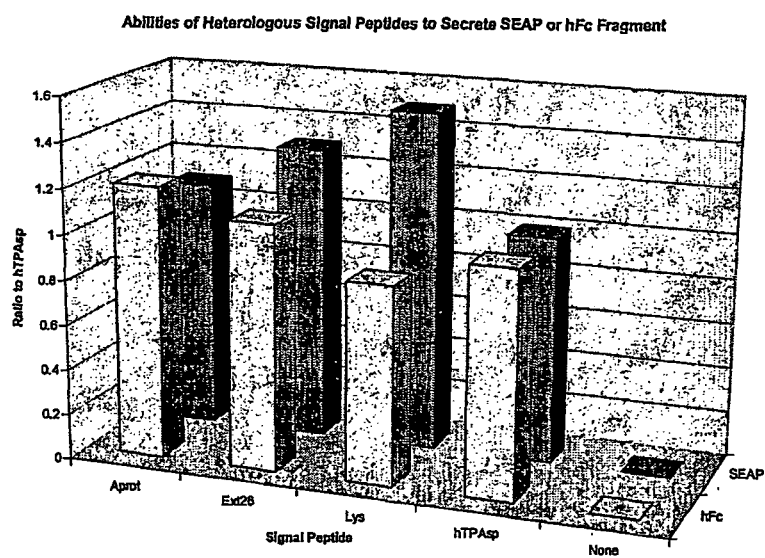
FIG. 6 shows the ability of heterologous signal peptides to direct secretion of SEAP or hFc fragment in B16 cells.

Addition of signal peptides from either bovine aprotinin, chicken lysozyme, or tobacco extensin to the N-terminus of mature SEAP allowed for efficient secretion of SEAP into cell media supernatants of both cell lines. Results for B16 cells are shown in FIG. 6.

Example 13

In-Vitro Analysis of Antigen Expression by Human IgG Fc Fragment Signal Peptide Panel SCC15 or B16 host cells were transfected as described in Example 9. The media supernatants were, removed from eighteen to forty hours after the media change.

ELISA plates (Costar) were incubated overnight at 4.degree. C. with 100.mu.l of goat anti-human IgG (Sigma #13382, 1/1000 dilution in carbonate coating buffer) per well. All subsequent incubations lasted 1 hour at room temperature with washes (10 mM Tris, 150 mM NaCl, 0.1% Brij-35, pH8.0) between each incubation. The wells were then blocked with 100.mu.l of 5% dry in PBS, followed by incubation with serially diluted media supernatants in dilution buffer (2% dry milk, PBS, 0.05% TWEEN®-20 polysorbate surfactant). This was followed by incubation with 100.mu.l of goat anti-human IgG/HRP (Sigma #A6029, 1/5000 dilution in dilution buffer) per well, followed by color development using 100.mu.l of TMB microwell substrate. The reactions were stopped with 100.mu.l of 1M H.sub.2SO.sub.4, and read at 450 nm. Data is presented as the ratio of the expression of the experimental signal peptides to the human TPA signal peptide vector.

Addition of signal peptides from either bovine aprotinin, chicken lysozyme, or tobacco extensin to the N-terminus of the human Fc fragment allowed for efficient secretion of hFc into cell media supernatants of both cell lines. Results for B16 cells are shown in FIG. 6.

Example 14

Use of the HBsAg, HSVgD and Flu-M2 Plasmid Expression Vectors for Immunisation of Mice a. Preparation of Cartridges of Immunisation For each plasmid to be tested, 25 mg of 2 micron gold powder was weighed into a microfuge tube. After the addition of a 250 µl aliquot of 50 mM spermidine (Aldrich Chemical, Inc, Milwaukee, Wis.), the tube was vortexed and briefly sonicated. The gold was microfuged out, and the spermidine replaced by a fresh 100 µl aliquot. The gold was resuspended by vortexing, after which 25 µg of DNA was added to the tube and mixed. While the tube was lightly vortexed, 100 µl of 10% CaCl (Fujisawa USA, Inc, Deerfield, Ill.) was added to precipitate the DNA onto the gold beads. The precipitation reaction was allowed to proceed for 10 minutes on the benchtop, after which the gold was collected by a brief microfuge spin and washed three times with absolute ethanol (Spectrum Quality Products, Inc, Gardena, Calif.) to remove excess precipitation reagents. The washed gold/DNA complex was then resuspended in 3.6 ml of 0.05 mg/ml polyvinylpyrrolidone (360 KD, Spectrum Quality Products, Inc, Gardena, Calif.) in absolute ethanol. This slurry was then injected into a Tefzelâ tube (McMaster-Carr, Chicago, Ill.) located in a tube turner (PowderJect Vaccines) which coats the inside of the Tefzelâ tube with the gold/DNA complex. After the tube turning procedure was completed, the tube was cut into 0.5" "shots" of vaccine which were loaded into the XR1 device (PowderJect Vaccines) for delivery to the mice.

b. Vaccination Procedure

Four to six week old mice were anesthetized with a mixture of Ketasetâ (Fort Dodge) and Rompunâ (Bayer). The bellies were shaved with a pair of electric clippers to remove hair, and two non-overlapping "shots" of vaccine were delivered via the XR1 device (450 psi) to the shaved area. The animals were returned to their cages and bled at six weeks post vaccination. Balb/c mice were used to evaluate the HBsAg expression vectors, and Swiss Webster mice were used to evaluate the HSV-gD and Flu M2 expression vectors.

Analysis of Sera for Anti-HBsAg Antibodies

Figure 7:
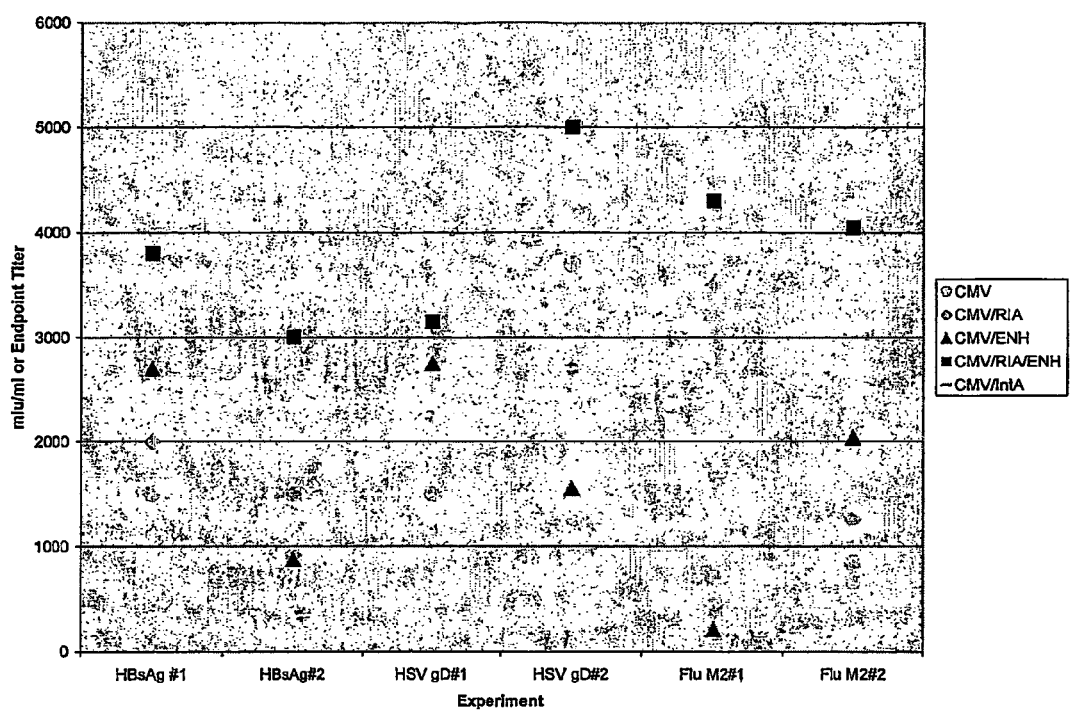
FIG. 7 illustrates levels of antibodies detected in the sera of mice immunised with antigen-encoding nucleic acids contained in a variety of plasmid expression vectors.
Figure 8:
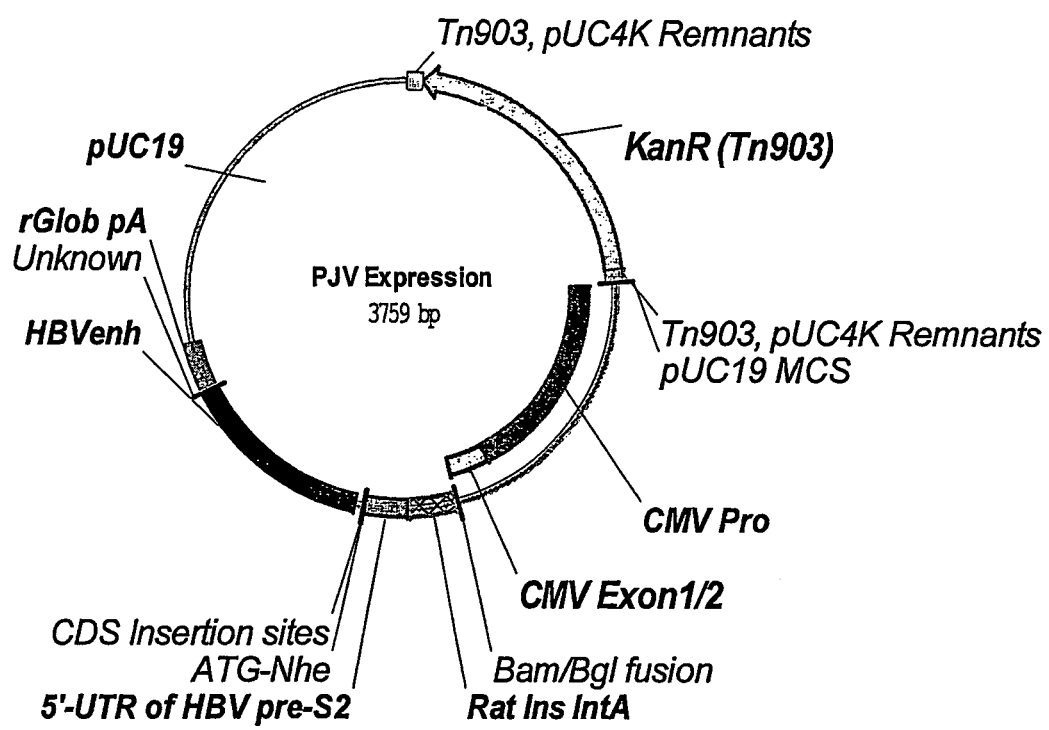
FIG. 8 is a diagrammatic representation of pJV expression vector.
Figure 9:
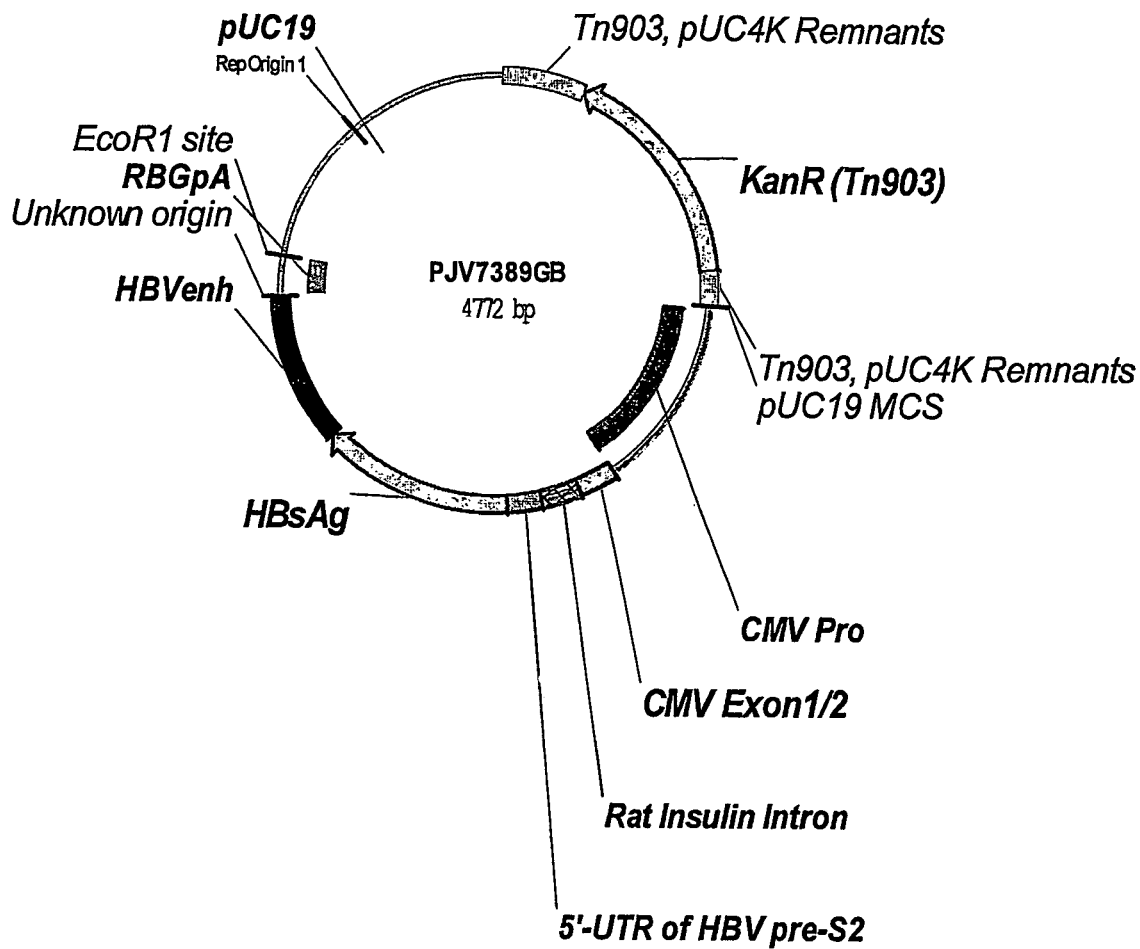
FIG. 9 is a diagrammatic representation of pJV7389.
Figure 10:
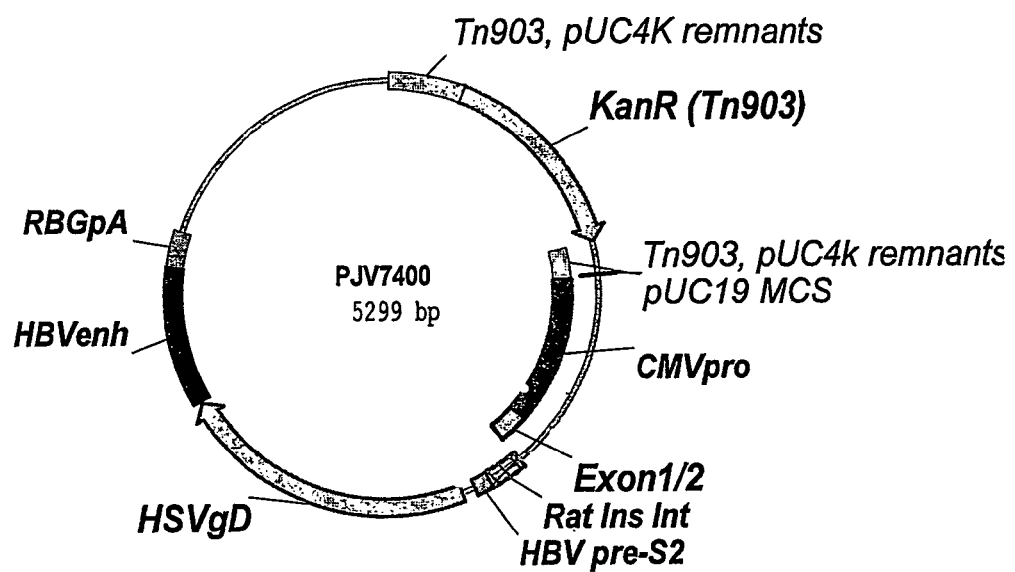
FIG. 10 is a diagrammatic representation of pJV7400.
Figure 11:
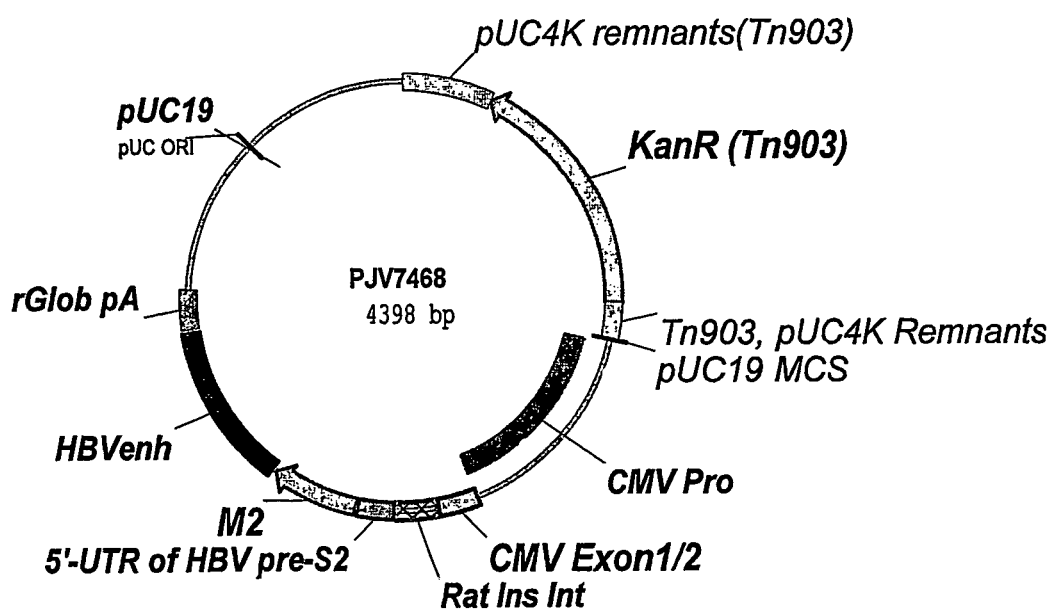
FIG. 11 is a diagrammatic representation of pJV7468.

At six weeks, blood samples were harvested from vaccinated animals. A volume of serum isolated from these samples was placed into wells of a reaction vessel supplied with the AUSAB®. EIA Diagnostic Kit (Abbott Laboratories, Abbott Park, Ill.). The volume of sera added depended upon the antibody titer of the sample, and the sample was diluted with sample dilution buffer to fall within values obtainable with a quantification panel. 200.mu.l from each vial of the AUSAB®. Quantification Panel (Abbott Laboratories, Abbott Park, Ill.) was added to wells of the reaction vessel. To each well a bead was added, after which the vessel was sealed and incubated for two hours at 40.degree. C. The wells were then washed of all liquid reaction components. To each washed well was added 200.mu.l of conjugate mix, after which the vessel was sealed and incubated for two hours at 40.degree. C. The wells were then washed of all liquid reaction components. The beads were transferred to new tubes after which 300.mu.l of color development buffer was added. At 30 minutes, the color development reaction was stopped by the addition of 1M sulfuric acid, and the absorbance of the reactions was measured at 490 nm in a QUANTUM II®. spectrophotometer (Abbott Laboratories, Abbott Park, Ill.). This spectrophotometer calculates the antibody levels of a sample by comparing the absorbance of the sample with a standard curve generated with the quantification panel. These antibody levels were then corrected for dilution factors. The data shown in FIG. 7 are the geometric mean titers of all animals vaccinated with a particular vector.

Analysis of Sera for Anti-Flu M2 Antigen Antibodies 96-well Costar medium-binding ELISA plates (Fisher Scientific, Pittsburgh, Pa.) were coated with a synthetic Flu M2 peptide (QCB/Biosource, Hopkinton, Mass.) at a concentration of 1 ug/ml in PBS (Biowhittaker, Walkerville, Md.) and incubated overnight at 4.degree. C. The plates were washed three times with 10 mM Tris (Sigma, St. Louis, Mo.)/150 mM NaCl (Fisher Scientific)/0.1% Brij-35. (Sigma), then blocked with 5% dry milk (Bio Rad Laboratories, Melville, N.Y.) in PBS for 1 hour at room temperature. All subsequent incubations were at room temperature for one hour and washes between each incubation were as stated above. Sample mouse sera, a standard (high titer, anti-M2 mouse sera) and a negative control (anti-HBsAg mouse sera) were diluted in 2% dry milk/PBS/0.05% TWEEN®-20 polysorbate surfactant (Sigma) and incubated in the ELISA plates. Goat anti-mouse IgG (H+L) biotin conjugated antibody (Southern Biotechnology Associate, Birmingham, Ala.) diluted 1:8000 in 2% dry milk/PBS/0.05% TWEEN®-20 polysorbate surfactant and streptavidin-horseradish peroxidase conjugate (Southern Biotechnology) diluted 1:8000 in PBS/0.1% TWEEN®-20 polysorbate surfactant followed. Color was developed using TMB substrate (BioFX, Owings Mills, Md.). The reactions were stopped with 1M H.sub.2SO.sub.4 and the plates read at 450 nm with an Emax precision microplate reader (Molecular Devices, Sunnyvale, Calif.). SoftMax Pro 4.1 software (Molecular Devices) was used to calculate endpoint titers using a four-parameter analysis. Titers were normalized to the standard serum, which had a pre-determined titer, to minimize assay-to-assay and plate-to-plate variation. Results are shown in FIG. 7.

Analysis of Sera for Anti-HSV gD Antigen Antibodies 96-well Costar medium-binding ELISA plates (Fisher Scientific, Pittsburgh, Pa.) were coated with HSV gD (Viral Therapeutics, Ithaca, N.Y.) protein at a concentration of 1 ug/ml in PBS (Biowhittaker, Walkerville, Md.) and incubated overnight at 4.degree. C. The plates were washed three times with 10 mM Tris (Sigma, St. Louis, Mo.)/150 mM NaCl (Fisher Scientific)/0.1% Brij-35 (Sigma), then blocked with 5% dry milk (Bio Rad Laboratories, Melville, N.Y.) in PBS for 1 hour at room temperature. All subsequent incubations were at room temperature for one hour and washes between each incubation were as stated above. Sample mouse sera, a standard (high titer, anti-gD mouse sera) and a negative control (anti HBsAg mouse sera) were diluted in 2% dry milk/ PBS/0.05% TWEEN-20 polysorbate surfactant (Sigma) and incubated in the ELISA plates. Goat anti-mouse IgG (H+L) biotin conjugated antibody (Southern Biotechnology Associate, Birmingham, Ala.) diluted 1:8000 in 2% dry milk/PBS/ 0.05% TWEEN-20 polysorbate surfactant and streptavidin-horseradish peroxidase conjugate (Southern Biotechnology) diluted 1:8000 in PBS/0.1% TWEEN-20 polysorbate surfactant followed. Color was developed using TMB substrate BioFX, Owings Mills, Md.). The reactions were stopped with 1M H.sub.2SO.sub.4 and the plates read at 450 nm with an Emax precision microplate reader (Molecular Devices, Sunnyvale, Calif.). SoftMax Pro 4.1 software (Molecular Devices) was used to calculate endpoint titers using a four-parameter analysis. Titers were normalized to the standard serum, which had a pre-determined titer, to minimize assay-to-assay and plate-to-plate variation. Results are shown in FIG. 7.

Accordingly, novel nucleic acid constructs, compositions comprising these constructs, and nucleic acid immunization techniques using these constructs have been described. Although preferred embodiments of the subject invention have been described in some detail, it is understood that obvious variations can be made without departing from the spirit and the scope of the invention as defined by the appended claims.

The invention claimed is:

1. A recombinant nucleic acid construct comprising:
   (i) a chimeric promoter sequence which consists of:
   (a) a human cytomegalovirus immediate early (hCMV IE) promoter sequence;
   (b) the nucleotide sequence of SEQ ID NO: 2; and
   (c) a heterologous intron, which is positioned 3' to the nucleotide sequence of SEQ ID NO:2;
   (ii) a coding sequence in operable linkage with the chimeric promoter;

(iii) a non-translated leader sequence which is selected from the group consisting of: a hepatitis B virus preS2 (HBVpreS2) antigen sequence, a HBV e-antigen sequence, and a Herpes Simples virus type 2 glycoprotein D (HSV type 2gD) antigen sequence, and which is in operable linkage with the chimeric promoter; and (iv) an enhancer sequence which is derived from a 3' untranslated region (UTR) of a hepatitis b surface antigen (HBsAg) sequence or of a simian cytomegalovirus (CMV) immediate early gene sequence, which is in operable linkage with the chimeric promoter and which is downstream of the coding sequence.

2. The recombinant nucleic acid construct according to claim 1, wherein:
the hCMV immediate early promoter sequence comprises SEQ ID NO:1;
the non-translated leader sequence is selected from the group consisting of: SEQ ID NO: 5, SEQ ID NO: 6, and SEQ ID NO:7;
the enhancer sequence is selected from the group consisting of: SEQ ID NO: 8 and SEQ ID NO: 9;
the heterologous intron is selected from the group consisting of: a rat insulin gene intron A sequence, a chicken keratin gene intron A sequence, and a chicken cardiac actin gene intron A sequence;
the construct further comprises a polyadenylation sequence; and
the construct further comprises a signal peptide.

3. The recombinant nucleic acid construct according to claim 2, wherein:
the rat insulin gene intron A sequence which comprises SEQ ID No: 3;
the polyadenylation sequence selected from the group consisting of: a rabbit B-globin gene, a human papilloma virus (HPV) early or late gene, a HSV-2 glycoprotein B (HSV-2gB) gene, a simian CMV immediate early gene, and a HSVgD late gene; and
the signal peptide is selected from the group consisting of: a human tissue plasminogen activator signal peptide (hTPAsp), an aprotinin signal peptide, a tobacco extensin signal peptide, and a chicken lysozyme signal peptide.

4. The recombinant nucleic acid construct according to claim 3, wherein the polyadenylation sequence is selected from the group consisting of: SEQ ID NO:10, SEQ ID NO:11, SEQ ID NO:12, and SEQ ID NO:13.

5. The recombinant nucleic acid construct according to claim 1, wherein the construct is a plasmid vector.

6. The recombinant nucleic acid construct according to claim 1, wherein the coding sequence of the nucleic acid construct encodes an antigen.

7. The recombinant nucleic acid construct according to claim 6, wherein the coding sequence encodes an antigen selected from the group consisting of a viral antigen, a bacterial antigen, a parasitic antigen, a fungal pathogen antigen, an allergy antigen, and a cancer antigen.

8. The recombinant nucleic acid construct according to claim 7, wherein the viral antigen is selected from the group consisting of an HPV antigen, a HIV antigen, a Herpes Simplex virus type 1 (HSV1) antigen, a HSV2 antigen, an influenza virus antigen, a Hepatitis A virus antigen and a Hepatitis B virus antigen.

9. The recombinant nucleic acid construct according to claim 8, wherein the antigen is HBsAg.

10. The recombinant nucleic acid construct according to claim 1, wherein the coding sequence encodes a polypeptide selected from the group consisting of: an ADP ribosylating bacterial subunit A, an ADP ribosylating bacterial subunit B, and both said subunits A and B.

11. The recombinant nucleic acid construct according to claim 10, wherein the bacterial subunit is selected from the group consisting of: Cholera toxin subunit A, Cholera toxin subunit B, *Escherichia coli* (*E. coli*) heat liable toxin subunit A, and (*E. coli*) heat labile toxin subunit B.

12. A composition comprising coated particles, suitable for delivery from a particle-mediated delivery device, which particles comprise carrier particles coated with the nucleic acid construct according to claim 1.

13. The composition comprising coated particles according to claim 12, wherein the carrier particles are gold or tungsten.

14. A dosage receptacle for a particle mediated delivery device comprising the composition comprising coated particles according to claim 13.

15. A particle mediated delivery device loaded with coated particles according to claim 13.

16. The particle mediated delivery device according to claim 15, which is a needleless syringe.

17. A pharmaceutical preparation comprising the nucleic acid construct according to claim 1, and a pharmaceutically acceptable excipient.

18. The pharmaceutical composition according to claim 17, wherein the composition is an immunogenic composition and the coding sequence of the nucleic acid construct encodes an antigen.

19. The pharmaceutical composition according to claim 18, wherein the composition further comprises an additional recombinant nucleic acid construct comprising a coding sequence which encodes a polypeptide selected from the group consisting of an adenosine diphosphate (ADP) ribosylating bacterial subunit A, an ADP ribosylating bacterial subunit B subunit, and both said subunits A and B.

20. A recombinant nucleic acid construct comprising a chimeric promoter sequence and a cloning site for insertion of a coding sequence in operable linkage with the chimeric promoter, wherein the chimeric promoter sequence consisting of:
(a) a hCMV immediate early promoter sequence;
(b) the nucleotide sequence of SEQ ID NO. 2; and
(c) a heterologous intron, which is positioned 3' to the nucleotide sequence of SEQ ID NO: 2.

21. A composition comprising coated particles, suitable for delivery from a particle-mediated delivery device, which particles comprise carrier particles coated with the recombinant nucleic acid construct according to claim 20.

22. A dosage receptacle for a particle mediated delivery device comprising coated particles according to claim 21.

23. A particle mediated delivery device loaded with coated particles according to claim 21.

24. A pharmaceutical preparation comprising the recombinant nucleic acid construct according to claim 20 and a pharmaceutically acceptable excipient.

25. A purified isolated chimeric promoter sequence which consists of:
(a) a hCMV immediate early promoter sequence;
(b) the nucleotide sequence of SEQ ID NO. 2; and
(c) a heterologous intron, which is positioned 3' to the nucleotide sequence of SEQ ID NO: 2.

* * * * *

UNITED STATES PATENT AND TRADEMARK OFFICE
CERTIFICATE OF CORRECTION

| | | |
|---|---|---|
| PATENT NO. | : 8,663,657 B2 | Page 1 of 1 |
| APPLICATION NO. | : 10/575087 | |
| DATED | : March 4, 2014 | |
| INVENTOR(S) | : Fuller | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2304 days.

Signed and Sealed this
Sixteenth Day of June, 2015

Michelle K. Lee
*Director of the United States Patent and Trademark Office*